(12) United States Patent
Yi et al.

(10) Patent No.: US 10,732,354 B2
(45) Date of Patent: Aug. 4, 2020

(54) SYSTEMS AND METHODS FOR FIBER-BASED VISIBLE AND NEAR INFRARED OPTICAL COHERENCE TOMOGRAPHY

(71) Applicant: BOSTON MEDICAL CENTER CORPORATION, Boston, MA (US)

(72) Inventors: Ji Yi, Brookline, MA (US); Weiye Song, Boston, MA (US)

(73) Assignee: BOSTON MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 16/433,954

(22) Filed: Jun. 6, 2019

(65) Prior Publication Data

US 2019/0377134 A1    Dec. 12, 2019

Related U.S. Application Data

(60) Provisional application No. 62/681,471, filed on Jun. 6, 2018.

(51) Int. Cl.
*G02B 6/293* (2006.01)
*A61B 3/10* (2006.01)
(Continued)

(52) U.S. Cl.
CPC .......... *G02B 6/29388* (2013.01); *A61B 3/102* (2013.01); *A61B 5/0066* (2013.01);
(Continued)

(58) Field of Classification Search
CPC ..... A61B 3/102; A61B 5/0066; A61B 5/0075; G02B 6/29388; G01B 9/02091;
(Continued)

(56) References Cited

U.S. PATENT DOCUMENTS 7,643,153 B2 *   1/2010   de Boer .............. A61B 5/0059
                                                              356/479
8,081,316 B2 *  12/2011   de Boer .............. A61B 3/1005
                                                              356/497

(Continued)

OTHER PUBLICATIONS

I. Itzkan, L. Qiu, H. Fang, M. M. Zaman, E. Vitkin, I. C. Ghiran, S. Salahuddin, M. Modell, C. Andersson, L. M. Kimerer, P. B. Cipolloni, K.-H, Lim, S. D. Freedman, I. Bigio, B. P. Sachs, E. B. Hanlon, and L. T. Perelman, "Confocal light absorption and scattering spectroscopic microscopy monitors organelles in live cells with no exogenous labels," PNAS 104, 17255-17260 (2007). (6 pages).

(Continued)

*Primary Examiner* — Dominic J Bologna
(74) *Attorney, Agent, or Firm* — Nixon Peabody LLP

(57) ABSTRACT

A system for analyzing a tissue sample includes two wavelength-division multiplexers and a fiber coupler. The first wavelength-division multiplexer combines visible and near infrared electromagnetic radiation and directs the combined electromagnetic radiation to the fiber coupler. The fiber coupler emits a sample beam of visible and near infrared electromagnetic radiation toward a tissue sample, and a reference beam of visible and near infrared electromagnetic radiation toward a reference mirror. The sample beam reflects off the tissue sample back to the fiber coupler. The reference beam reflects off the reference mirror back to the fiber coupler. The fiber coupler combines the reflected sample and reference beams and directs the combined electromagnetic radiation to the second wavelength-division multiplexer. The second wavelength-division multiplexer sends visible electromagnetic radiation from the sample and reference beams to a first spectrometer, and near infrared electromagnetic radiation from the sample and reference beams to a second spectrometer.

30 Claims, 18 Drawing Sheets
(4 of 18 Drawing Sheet(s) Filed in Color)

(51) Int. Cl.
  *H04J 14/02* (2006.01)
  *G01B 9/02* (2006.01)
  *G01N 21/359* (2014.01)
  *G01N 21/47* (2006.01)
  *A61B 5/00* (2006.01)
(52) U.S. Cl.
  CPC ....... *G01B 9/02091* (2013.01); *G01N 21/359* (2013.01); *G01N 21/474* (2013.01); *H04J 14/02* (2013.01); *G01N 2021/4761* (2013.01)
(58) Field of Classification Search
  CPC .............. G01N 21/359; G01N 21/474; G01N 2021/4761; H04J 14/02; G01D 5/266; G01D 5/268
  See application file for complete search history.

(56) References Cited

U.S. PATENT DOCUMENTS

| | | | | |
|---|---|---|---|---|
| 8,687,666 | B2* | 4/2014 | Goldberg | G01N 21/4795 372/99 |
| 9,330,092 | B2* | 5/2016 | Vakoc | A61B 3/102 |
| 10,052,019 | B1* | 8/2018 | Jiao | A61B 5/0071 |
| 2003/0227631 | A1* | 12/2003 | Rollins | G01B 9/02045 356/479 |
| 2007/0024856 | A1* | 2/2007 | Izatt | A61B 3/102 356/456 |
| 2008/0285043 | A1 | 11/2008 | Fercher | |
| 2011/0228223 | A1* | 9/2011 | Jiao | A61B 3/102 351/206 |
| 2015/0077755 | A1 | 3/2015 | Yun | |
| 2015/0168126 | A1 | 6/2015 | Nevet | |
| 2015/0348287 | A1* | 12/2015 | Yi | G06T 11/003 382/131 |
| 2016/0313112 | A1* | 10/2016 | Yamanari | A61B 3/102 |
| 2016/0345820 | A1 | 12/2016 | Frisken | |
| 2017/0027438 | A1 | 2/2017 | Uhlhorn | |
| 2017/0035291 | A1* | 2/2017 | Jiao | A61B 3/102 |
| 2017/0311797 | A1* | 11/2017 | Kuo | A61B 3/1233 |
| 2019/0014983 | A1 | 1/2019 | Chong | |
| 2019/0223729 | A1* | 7/2019 | Frisken | A61B 3/00 |

OTHER PUBLICATIONS

N. N. Boustany, S. A. Boppart, and V. Backman, "Microscopic Imaging and Spectroscopy with Scattered Light," Annu. Rev. Biomed Eng 12, 285-314 (2010). (32 pages).
J. Kwon, M. Kim, H. Park, B.-M. Kang, Y. Jo, J.-H. Kim, O. James, S.-H. Yun, S.-G, Kim, M. Suh, and M. Choi, "Label-free nanoscale optical metrology on myelinated axons in vivo," Nat. Commun. 8, 1832 (2017). (9 pages).
J. Yi, A. J. Radosevich, J. D. Rogers, S. C. P. Norris, 1. R. Çapo?lu, A. Taflove, and V. Backman, "Can OCT be sensitive to nanoscale structural alterations in biological tissue?" Opt. Express 21, 9043-9059 (2013). (17 pages).
L. Cherkezyan, I. Capoglu, H. Subramanian, J. D. Rogers, D. Damania, A. Taflove, and V. Backman, "Interferometric Spectroscopy of Scattered Light Can Quantify the Statistics of Subdiffractional Refractive-Index Fluctuations," PRL 111, 033903 (2013). (5 pages).
R. Barer and S. Tkaczyk, "Refractive index of concentrated protein solutions," Nature 173 (4409) (1954). (2 pages).
H. G. Davies, M. H. F. Wilkins, J. Chayen, and L. F. La Cour, "The Use of the Interference Microscope to Determine Dry Mass in Living Cells and as a Quantitative Cytochemical Method," Quarterly Journal of Microscopical Science s3-95, 271-304 (1954). (38 pages).
T. A. Zangle and M. A. Teitell, "Live-cell mass profiling: an emerging approach in quantitative biophysics," Nature Methods 11, 1221 (2014). (8 pages).

L. Cherkezyan, H. Subramanian, and V. Backman, "What structural length scales can be detected by the spectral variance of a microscope image?," Opt. Lett. 39, 4290-4293 (2014). (11 pages).
A. J. Radosevich, J. Yi, J. D. Rogers, and V. Backman, "Structural length-scale sensitivities of reflectance measurements in continuous random media under the Born approximation," Opt. Lett. 37, 5220-5222 (2012). (11 pages).
M. Hunter, V. Backman, G. Popescu, M. Kalashnikov, C. W. Boone, A. Wax, V. Gopal, K. Badizadegan. G. D. Stoner, and M. S. Feld, "Tissue Self-Affinity and Polarized Light Scattering in the Born Approximation: A New Model for Precancer Detection," PRL 97, 138102 (2006). (4 pages).
N. G. Terry, Y. Zhu, M. T. Rinehart, W. J. Brown, S. C. Gebhart, S. Bright, E. Carretta, C. G. Ziefle, M. Panjehpour, J. Galanko, R. D. Madanick, E. S. Dellon, D. Trembath, A. Bennett, J. R. Goldblum, B. F. Overholt, J. T. Woosley, N. J. Shaheen, and A. Wax, "Detection of Dysplasia in Barrett's Esophagus With In Vivo Depth-Resolved Nuclear Morphology Measurements," Gastroenterology 140, 42-50 (2011). (19 pages).
L. Qiu, D. K. Pleskow, R. Chuttani. E. Vitkin, J. Leyden, N. Ozden, S. Itani, L. Guo, A. Sacks, J. D. Goldsmith, M. D. Modell, E. B. Hanlon, I. Itzkan, and L. T. Perelman, "Multispectral scanning during endoscopy guides biopsy of dysplasia in Barrett's esophagus," Nat Med 16, 603-606 (2010). (5 pages).
Y. Zhu, T. Fearn, G. Mackenzie, I. J. Bigio, S. G. Bown, L. B. Lovat, B. Clark, and J. M. Dunn, "Elastic scattering spectroscopy for detection of cancer risk in Barrett's esophagus: experimental and clinical validation of error removal by orthogonal subtraction for increasing accuracy," J. Biomed. Opt 14, 044022-044022-044027 (2009). (7 pages).
Y. N. Mirabal, S. K. Chang, E. N. Atkinson, A. Malpica, M. Follen, and R. Richards-Kortum, "Reflectance spectroscopy for in vivo detection of cervical precancer," J. Biomed. Opt 7, 587-594 (2002). (8 pages).
M. Canpolat, A. Akman-Karakş, G. A. Gökhan-Ocak, I. C. Başsorgun, M. Akif Çiftçioğlu, and E. Alpsoy, "Diagnosis and Demarcation of Skin Malignancy Using Elastic Light Single-Scattering Spectroscopy: A Pilot Study," Dermatologic Surgery 38, 215-223 (2012), (9 pages).
C. P. Fleming, J. Eckert, E. F. Halpern, J. A. Gardecki, and G. J. Tearney, "Depth resolved detection of lipid using spectroscopic optical coherence tomography," Biomed. Opt. Express 4, 1269-1284 (2013). (16 pages).
A. Lichtenegger, D. J. Harper, M. Augustin, P. Eugui, M. Muck, J. Gesperger, C. K. Hitzenberger, A. Woehrer, and B. Baumann, "Spectroscopic imaging with spectral domain visible light optical coherence microscopy in Alzheimer's disease brain samples," Biomed. Opt. Express 8, 4007-4025 (2017). (19 pages).
J. R. Maher, V. Jaedicke, M. Medina, H. Levinson, M. A. Selim, W. J. Brown, and A. Wax, "In vivo analysis of burns in a mouse model using spectroscopic optical coherence tomography," Opt. Lett 39, 5594-5597 (2014). (13 pages).
X.-R. Huang, Y. Zhou, W. Kong, and R. W. Knighton, "Reflectance Decreases before Thickness Changes in the Retinal Nerve Fiber Layer in Glaucomatous Retinas," IOVS 52, 6737-6742 (2011). (6 pages).
X.-R. Huang, Y. Zhou, R. W. Knighton, W. Kong, and W. J. Feuer, "Wavelength-Dependent Change of Retinal Nerve Fiber Layer Reflectance in Glaucomatous Retinas," IOVS 53, 5869-5876 (2012). (8 pages).
A. Hajiaboli and M. Popovic, "Human Retinal Photoreceptors: Electrodynamic Model of Optical Microfilters," IEEE J. of Sel. Top. Quantum Electron. 14, 126-130 (2008). (5 pages).
B. Vohnsen, "Directional sensitivity of the retina: A layered scattering model of outer-segment photoreceptor pigments," Biomed. Opt. Express 5, 1569-1587 (2014). (19 pages).
Q. V. Hoang, R. A. Linsenmeier, C. K. Chung, and. C. A. Curcio, "Photoreceptor inner segments in monkey and human retina: Mitochondrial density, optics, and regional variation," Visual Neuroscience 19, 395-407 (2002). (13 pages).
A. M. Labin, S. K. Safuri, E. N. Ribak, and I. Perlman, "Müller cells separate between wavelengths to improve day vision with minimal effect upon night vision," Nat. Commun 5, 4319 (2014). (9 pages).

(56) References Cited

OTHER PUBLICATIONS

W. Song, L. Zhang, S. Ness, and J. Yi, "Wavelength-dependent optical properties of melanosomes in retinal pigmented epithelium and their changes with melanin bleaching: a numerical study," Biomed. Opt. Express 8, 3966-3980 (2017). (15 pages).
D. Huang, E. Swanson, C. Lin, J. Schuman, W. Stinson, W. Chang, M. Hee, T. Flotte, K. Gregory, C. Puliafito, and a. et, "Optical coherence tomography," Science 254, 1178-1181 (1991). (12 pages).
U. Morgner, W. Drexler, F. Kärtner, X. Li, C. Pitris, E. Ippen, and J. Fujimoto, "Spectroscopic optical coherence tomography," Opt. Lett 25, 111-113 (2000). (3 pages).
J. Yi and V. Backman, "Imaging a fill set of optical scattering properties of biological tissue by inverse spectroscopic optical coherence tomography," Opt. Lett 37, 4443-4445 (2012). (8 pages).
J. Yi, Q. Wei, W. Liu, V. Backman, and. H. F. Zhang, "Visible-light optical coherence tomography for retinal oximetry," Opt. Lett 38, 1796-1798 (2013). (9 pages).
J. Yi, S. Chen, X. Shu, A. A. Fawzi, and H. F. Zhang, "Human retinal imaging using visible-light optical coherence tomography guided by scanning laser ophthalmoscopy," Biomed. Opt. Express 6, 3701-3713 (2015).
F. E. Robles, C. Wilson, G. Grant, and A. Wax, "Molecular imaging true-colour spectroscopic optical coherence tomography," Nat Photon 5, 744-747 (2011). (10 pages).
X. Zhang, J. Hu, R. W. Knighton, X.-R. Huang, C. A. Puliafito, and S. Jiao, "Dual-band spectral-domain optical coherence tomography for in vivo imaging the spectral contrasts of the retinal nerve fiber layer," Opt. Express 19, 19653-19659 (2011). (7 pages).
S. P. Chong, M. Bernucci, H. Radhakrishnan, and V. J. Srinivasan, "Structural and functional human retinal imaging with a fiber-based visible light OCT ophthalmoscope," Biomed. Opt. Express 8, 323-337 (2017). (15 pages).
S. Chen, X. Shu, J. Yi, A. A. Fawzi, and H. F. Zhang, "Dual-band optical coherence tomography using a single supercontinuum laser source," J. Biomed. Opt. 21(6), 066013 (2016). (8 pages).
R. J. Zawadzki, B. Cense, Y. Zhang, S. S. Choi, D. T. Miller, and J. S. Werner, "Ultrahigh-resolution optical coherence tomography with monochromatic and chromatic aberration correction," Opt. Express 16, 8126-8143 (2008). (19 pages).
A. Dubra and Y. Sulai, "Reflective afocal broadband adaptive optics scanning ophthalmoscope," Biomed. Opt. Express 2, 1757-1768 (2011). (12 pages).
F. LaRocca, D. Nankivil, S. Farsiu, and J. A. Izatt, "True color scanning laser ophthalmoscopy and optical coherence tomography handheld probe," Biomed. Opt. Express 5, 3204-3216 (2014). (13 pages).
R. Watkins, "Zemax Models of the Human Eye" (2013), retrieved http://customer.zemax.com/os/resources/learn/knowledgebase/zemax-models-of-the-human-eye. (12 pages).
F. C. Delori, R. H. Webb, and D. H. Sliney, "Maximum permissible exposures for ocular safety (ANSI 2000), with emphasis on ophthalmic devices," JOSA A 24, 1250-1265 (2007). (16 pages).
N. Otsu, "A threshold selection method from gray-level histograms," IEEE Transactions on Systems, Man and Cybernetics 9, 62-66 (1979). (5 pages).
L. Scolaro, R. A. McLaughlin, B. R. Klyen, B. A. Wood, P. D. Robbins, C. M. Saunders, S. L. Jacques, and D. D. Sampson, "Parametric imaging of the local attenuation coefficient in human axillary lymph nodes assessed using optical coherence tomography," Biomed. Opt. Express 3, 366-379 (2012). (14 pages).
R. Liu, G. Spicer, S. Chen, H. F. Zhang, J. Yi, and V. Backman, "Theoretical model for optical oximetry at the capillary level: exploring hemoglobin oxygen saturation through backscattering of single red blood cells," J. Biomed. Opt. 22(2) (2017). (9 pages).
D. J. Faber, M. C. G. Aalders, E. G. Mik, B. A. Hooper, M. J. C. van Gemert, and T. G. van Leeuwen, "Oxygen Saturation-Dependent Absorption and Scattering of Blood," PRL 93, 028102 (2004). (4 pages).

C. N. Keilhauer and F. o. C. Delori, "Near-Infrared Autofluorescence Imaging of the Fundus: Visualization of Ocular Melanin," IOVS 47. 3556-3564 (2006). (9 pages).
J. D. Rogers, A. J. Radosevich, Y. Ji, and V. Backman, "Modeling Light Scattering in Tissue as Continuous Random Media Using a Versatile Refractive Index Correlation Function," IEEE J. Sel. Top. Quantum Electron. 20. 173-186 (2014). (14 pages).
X.R. Huang, R. W. Knighton, Y. Z. Spector, J. Qiao, W. Kong, and Q. Zha , "Reflectance Spectrum and Birefringence of the Retinal Nerve Fiber Layer With Hypertesive Damage of Axonal Cytoskeleton," IOVS 58, 2118-2129 (2017). (12 pages).
X.-R. Huang, R. W. Knighton, and L. N. Cavuoto, "Microtubule Contribution to the Reflectance of the Retinal Nerve Fiber Layer," IOVS 47, 5363-5367 (2006). (5 pages).
J. Yi, Z. Puyang, L. Feng, L. Duan, P. Liana, V. Backman, X. Liu, and H. F. Zhang, "Optical Detection of Early Damage in Retinal Ganglion Cells in a Mouse Model of Partial Optic Nerve Crush Injury," IOVS 57, 5665-5671 (2016). (7 pages).
A. Hajiaboli and M. Popovie, "FDTD Analysis of Light Propagation in the Human Photoreceptor Cells," IEEE Transactions on Magnetics 44, 1430-1433 (2008). (4 pages).
Gomes AJ, Roy HK, Turzhitsky V, et al. Rectal Mucosal Microvascular Blood Supply Increase Is Associated with Colonic Neoplasia. Clinical Cancer Research 2009;15:3110-7. (9 pages).
Roy HK, Gomes A, Turzhisky V, et al. Biophotonic detection of increased microvascular blood content (EIBS) as a marker of field carcinogenesis detection: Potential adjunctive technology for Colonoscopy. Gastrointestinal Endoscopy 2008;67:Ab131-Ab. (7 pages).
Roy HK, Gomes AJ, Ruderman S, et al. Optical measurement of rectal microvasculature as an adjunct to flexible sigmoidosocopy: gender-specific implications. Cancer Prev Res (Phila) 2010;3:844-51. (9 pages).
Tiwari AK, Crawford SE, Radosevich A, et al. Neo-angiogenesis and the premalignant micro-circulatory augmentation of early colon carcinogenesis. Cancer Lett 2011;306:205-13 (9 pages).
Wali RK, Roy HK, Kim YL, et al. Increased microvascular blood content is an early event in colon carcinogenesis. Gut 2005;54:654-60. (7 pages).
Roy HK, Wali RK, Kim Y, et al. Inducible nitric oxide synthase (iNOS) mediates the early increase of blood supply (EIBS) in colon carcinogenesis. FEBS Letters 2007;581:3857-62. (12 pages).
Roy HK, Wali RK, Koetsier J, et al. Increased mucosal blood supply is an early preneoplastic marker in colon neoplasia. Gastroenterology 2004,126:A38-A. (11 pages).
Mart Dela Cruz SL, Sanjib Chowdhury, Ashish K. Tiwari, Navneet Momi, Ramesh K. Wali, Charles Bliss, Christopher Huang, David Lichtenstein, Swati Bhattacharya, Anisha Varma-Wilson, Vadim Backman and Hemant K. Roy. Metabolic Reprogramming of the Premalignant Colonic Mucosa is an Early Event in Carcinogenesis. Oncotarget 2017;8:20543-57. (15 pages).
Jia Y, Ma Z, Liu X, et al. Metformin prevents DMH-induced colorectal cancer in diabetic rats by reversing the warburg effect. Cancer Med 2015;4:1730-41. (12 pages).
Harada K, Ferdous T, Harada T, Ueyama Y. Metformin in combination with 5-fluorouracil suppresses tumor growth by inhibiting the Warburg effect in human oral squamous cell carcinoma. Int J Oncol 2016;49:276-84. (9 pages).
Kim S, Thyokawa H, Yamao J, et al. Antitumor effect of angiotensin II type 1 receptor blocker losartan for orthotopic rat pancreatic adenocarcinoma. Pancreas 2014;43:886-90. (6 pages).
Azoulay L, Assimes TL, Yin H, Bartels DB, Schiffrin EL, Suissa. S. Long-term use of angiotensin receptor blockers and the risk of cancer. PLoS One 2012;7:e50893. (8 pages).
Hallas J, Christensen R, Andersen M, Friis S, Bjerrum L. Long term use of drugs affecting the renin-angiotensin system and the risk of cancer: a population-based case-control study. Br J Clin Pharmacol 2012;74:180-8. (9 pages).
Cardwell CR, Mc Menamin UC, Hicks BM, Hughes C, Cantwell MM, Murray LJ. Drugs affecting the renin-angiotensin system and survival from cancer: a population based study of breast, colorectal and prostate cancer patient cohorts. BMC Med 2014;12:28. (15 pages).

(56) References Cited

OTHER PUBLICATIONS

Makar GA, Holmes JH, Yang YX. Angiotensin-converting enzyme inhibitor therapy and colorectal cancer risk. J Natl Cancer Inst 2014;106:djt374. (8 pages).
Dai YN, Wang JH, Zhu JZ, Lin JQ, Yu CH, Li YM. Angiotensin-converting enzyme inhibitors/angiotensin receptor blockers therapy and colorectal cancer: a systematic review and meta-analysis. Cancer Causes Control 2015;26:1245-55. (11 pages).
Wang KL, Liu CJ, Chao TF, et al. Long-term use of angiotensin II receptor blockers and risk of cancer: a population-based cohort analysis. Int J Cardiol 2013;167:2162-6. (5 pages).
Siegel RL, Miller KD, Fedewa SA, et al. Colorectal cancer statistics, 2017. CA Cancer J Clin 2017. (17 pages).
Allott EH, Oliver E, Lysaght J, et al. The SGBS cell strain as a model for the in vitro study of obesity and cancer. Clin Transl Oncol 2012;14:774-82. (9 pages).
Levin B, Lieberman DA, McFarland B, et al. Screening and surveillance for the early detection of colorectal cancer and adenomatous polyps, 2008: a joint guideline from the American Cancer Society, the US Multi-Society Task Force on Colorectal Cancer, and the American College of Radiology. Gastroenterology 2008;134:1570-95. (31 pages).
Levin B, Lieberman DA, McFarland B, et al. Screening and surveillance for the early detection of colorectal cancer and adenomatous polyps, 2008: a joint guideline from the American Cancer Society, the US Multi-Society Task Force on Colorectal Cancer, and the American College of Radiology. CA Cancer J Clin 2008;58:130-60. (31 pages).
Lieberman DA. Clinical practice. Screening for colorectal cancer. N Engl J Med 2009;361:1179-87. (9 pages).
Qaseem A, Denberg TD, Hopkins RH, Jr., et al. Screening for colorectal cancer: a guidance statement from the American College of Physicians. Ann Intern Med 2012;156:378-86. (11 pages).
Whitlock EP, Lin JS, Liles E, Beil TL, Fu R. Screening for colorectal cancer: a targeted, updated systematic review for the U.S. Preventive Services Task Force. Ann Intern Med 2008;149:638-58. (27 pages).
Imperiale TF, Ransohoff DF, Itzkowitz SH. Multitarget stool DNA testing for colorectal-cancer screening. N Engl J Med 2014;371:187-8. (5 pages).
Johnson CD, Chen MH, Toledano AY, et al. Accuracy of CT colonography for detection of large adenomas and cancers. N Engl J Med 2008;359:1207-17. (15 pages).
Jin P, Kang Q, Wang X, et al. Performance of a second-generation methylated SEPT9 test in detecting colorectal neoplasm. J Gastroenterol Hepatol 2015;30:830-3. (4 pages).
Backman V, Roy HK. Light-scattering technologies for field carcinogenesis detection: a modality for endoscopic prescreening. Gastroenterology 2010;140:35-41. (14 pages).
Backman V, Roy HK. Advances in Biophotonics Detection of Field Carcinogenesis for Colon Cancer Risk Stratification. Journal of Cancer 2013;4:251-61. (11 pages).
Chai H, Brown RE. Field effect in cancer—an update. Ann Clin Lab Sci 2009;39:331-7, (8 pages).
Takayama T, Katsuki S, Takahashi Y, et al. Aberrant crypt foci of the colon as precursors of adenoma and cancer. N Engl J Med 1998;339:1277-84. (8 pages).
Lewis JD, Ng K, Hung KE, et al. Detection of proximal adenomatous polyps with screening sigmoidoscopy: a systematic review and meta-analysis of screening colonoscopy. Arch Intern Med 2003;163:413-20. (8 pages).
Alberts DS, Einspahr JG, Krouse RS, et al. Karyometry of the colonic mucosa. Cancer Epidemiol Biomarkers Prev 2007;16:2704-16. (14 pages).
Bernstein C, Bernstein H, Payne CM, Dvorak K, Garewal H. Field defects in progression to gastrointestinal tract cancers. Cancer Lett 2008;260:1-10. (14 pages).

Worthley DL, Whitehall VL, Buttenshaw RL, et al. DNA methylation within the normal colorectal mucosa is associated with pathway-specific predisposition to cancer. Oncogene 2010;29:1653-62. (10 pages).
Luo Y, Yu M, Grady WM. Field cancerization in the colon: a role for aberrant DNA methylation? Gastroenterol Rep (Oxf) 2014;2:16-20. (5 pages).
Kunte DP, DelaCruz M, Wali RK, et al. Dysregulation of MicroRNAs in Colonic Field Carcinogenesis: Implications for Screening. Plos One 2012;7. (8 pages).
Grady WM, Parkin RK, Mitchell PS, et al. Epigenetic silencing of the intronic microRNA hsa-miR-342 and its host gene EVL in colorectal cancer. Oncogene 2008;27:3880-8. (9 pages).
McGarrity TJ, Peiffer LP. Protein kinase C activity as a potential marker for colorectal neoplasia. Dig Dis Sci 1994;39:458-63. (6 pages).
Vucenik I, Gotovac J, Druzijanic N, Shamsuddin AM. Usefulness of galactose oxidase-Schiff test in rectal mucus for screening of colorectal malignancy. Anticancer Res 2001;21:1247-55. (10 pages).
Anti M, Marra G, Armelao F, et al. Rectal epithelial cell proliferation patterns as predictors of adenomatous colorectal polyp recurrence. Gut 1993;34:525-30. (6 pages).
Bernstein C, Bernstein H, Garewal H, et al. A bile acid-induced apoptosis assay for colon cancer risk and associated quality control studies. Cancer Res 1999;59:2353-7. (6 pages).
Regge D, Laudi C, Galatola G, et al. Diagnostic accuracy of computed tomographic colonography for the detection of advanced neoplasia in individuals at increased risk of colorectal cancer. Jama 2009;301:2453-61. (9 pages).
Polley AC, Mulholland F, Pin C, et al. Proteomic analysis reveals field-wide changes in protein expression in the morphologically normal mucosa of patients with colorectal neoplasia . . . . Cancer research 2006;66:6553-62. (11 pages).
Daniel CR, Bostick RM, Flanders WD, et al. TGF-alpha expression as a potential biomarker of risk within the normal-appearing colorectal mucosa of patients with and without incident sporadic adenoma. Cancer Epidemiol Biomarkers Prev 2009;18:65-73. (19 pages).
Keku TO, Sandler RS, Simmons JG, et al. Local IGFBP-3 mRNA expression, apoptosis and risk of colorectal adenomas. BMC Cancer 2008;8:143. (9 pages).
Mucci LA, Hjelmborg JB, Harris JR, et al. Familial Risk and Heritability of Cancer Among Twins in Nordic Countries. JAMA 2016;315:68-76. (18 pages).
Chubak J. Kamineni A. Buist DSM, Anderson ML, Whitlock EP. Aspirin Use for the Prevention of Colorectal Cancer: An Updated Systematic Evidence Review for the US Preventive Services Task Force. Rockville (MD)2015. (127 pages).
Force USPST. Routine aspirin or nonsteroidal anti-inflammatory drugs for the primary prevention of colorectal cancer: U.S. Preventive Services Task Force recommendation statement. Ann Intern Med 2007;146:361-4. (5 pages).
Bertagnolli MM, Eagle CJ, Lauber AG, et al. Celecoxib for the prevention of sporadic colorectal adenomas. N Engl J Med 2006;355:873-84. (12 pages).
Solomon SD, McMurray JJ, Pfeffer MA, et al. Cardiovascular risk associated with celecoxib in a clinical trial for colorectal adenoma prevention. N Engl J Med 2005;352:1071-80, (10 pages).
Bresalier RS, Sandler RS, Quan H, et al. Cardiovascular events associated with rofecoxib in a colorectal adenoma chemoprevention trial. N Engl J Med 2005;352:1092-102. (11 pages).
Chan AT, Giovannucci EL, Meyerhardt JA, Schernhammer ES, Curhan GC, Fuchs CS. Long-term use of aspirin and nonsteroidal anti-inflammatory drugs and risk of colorectal cancer. JAMA 2005;294:914-23. (20 pages).
Baron JA, Cole BF, Sandler RS, et al. A randomized trial of aspirin to prevent colorectal adenomas. N Engl J Med 2003;348:891-9, (9 pages).
Sandler RS, Halabi S, Baron JA, et al. A randomized trial of aspirin to prevent colorectal adenomas in patients with previous colorectal cancer, N Engl J Med 2003;348:883-90. (8 pages).
Nan H, Hutter CM, Lin Y, et al. Association of aspirin and NSAID use with risk of colorectal cancer according to genetic variants. JAMA 2015;313:1133-42. (18 pages).

(56) References Cited

OTHER PUBLICATIONS

Pommergaard HC, Burcharth J, Rosenberg J, Raskov H. Aspirin, Calcitriol, and Calcium Do Not Prevent Adenoma Recurrence in a Randomized Controlled Trial. Gastroenterology 2016:150:114-22 e4. (13 pages).
Cairns RA, Harris I, McCracken S, Mask TW. Cancer cell metabolism. Cold Spring Harb Symp Quant Biol 2011;76:299-311. (13 pages).
Hanahan D, Weinberg RA. Hallmarks of cancer: the next generation. Cell 2011, 144:646-74. (29 pages).
Warburg O. On origin of cancer cells. Science 1956;123:309-14. (7 pages).
Ward PS, Thompson CB. Metabolic reprogramming: a cancer hallmark even warburg did not anticipate. Cancer Cell 2012;21:297-308. (30 pages).
Bultman SJ. The microbiome and its potential as a cancer preventive intervention. Semin Oncol 2016;43:97-106. (23 pages).
Hagland HR, Soreide K. Cellular metabolism in colorectal carcinogenesis: Influence of lifestyle, gut microbiome and metabolic pathways. Cancer Lett 2015;356:273-80. (8 pages).
Higurashi T, Hosono K, Takahashi H, et al. Metformin for chemoprevention of metachronous colorectal adenoma or polyps in post-polypectomy patients without diabetes: a multicentre double-blind, placebo-controlled, randomised phase 3 trial. Lancet Oncol 2016;17:475-83. (9 pages).
Abdelsatir AA, Husain NE, Hassan AT, Elmadhoun WM, Almobarak AO, Ahmed MH. Potential Benefit of Metformin as Treatment for Colon Cancer: the Evidence so Far. Asian Pac J Cancer Prev 2015;16:8053-8. (7 pages).
Schuster S, Boley D, Moller P, Stark H, Kaleta C. Mathematical models for explaining the Warburg effect: a review focussed on ATP and biomass production. Biochem Soc Trans 2015;43:1187-94. (8 pages).
Raica M, Cimpean AM, Ribatti D. Angiogenesis in pre-malignant conditions. Eur J Cancer 2009;45:1924-34. (11 pages).
Teo NB, Shoker BS, Martin L, Sloane JP, Holcombe C. Angiogenesis in pre-invasive cancers. Anticancer Res 2002;22:2061-72. (1 page).
Shpitz B, Gochberg S, Neufeld D, et al. Angiogenic switch in earliest stages of human colonic tumorigenesis. Anticancer Res 2003;23:5153-7. (1 page).
Tiwari AK, Crawford SE, Radosevich A, et al. Neo-angiogenesis and the premalignant micro-circulatory augmentation of early colon carcinogenesis. Cancer Letters 2011;306:205-13. (9 pages).
Backman V, Roy HK. Light-scattering technologies for field carcinogenesis detection: a modality for endoscopic prescreening. Gastroenterology 2011;140:35-41. (14 pages).
Guda K, Veigl ML, Varadan V, et al. Novel recurrently mutated genes in African American colon cancers. Proc Natl Acad Sci U S A 2015;112:1149-54. (6 pages).
Wali RK, Momi N, Dela Cruz M, et al. Higher Order Chromatin Modulator Cohesin SA1 is an Early Biomarker for Colon Carcinogenesis: Race-Specific Implications. Cancer Prev Res (Phila) 2016;9:844-54. (22 pages).
Roy HK, Bianchi LK. Differences in colon adenomas and carcinomas among women and men: potential clinical implications. JAMA 2009;302:1696-7. (4 pages).
Zhou B, Shu B, Yang J, Liu J, Xi T, Xing Y. C-reactive protein, interleukin-6 and the risk of colorectal cancer: a meta-analysis. Cancer Causes Control 2014;25:1397-405. (9 pages).
Patel M, Gomes A, Ruderman S, et al. Polarization gating spectroscopy of normal-appearing duodenal mucosa to detect pancreatic cancer. Gastrointestinal Endoscopy 2014;80:786-+. (20 pages).
Radosevich AJ, Turzhitsky VM, Mutyal NN, et al. Depth-resolved measurement of mucosal microvascular blood content using low-coherence enhanced backscattering spectroscopy. Biomedical Optics Express 2010:1:1196-208. (13 pages).
Roy HK, Gomes A, Turzhitsky V, et al. Spectroscopic microvascular blood detection from the endoscopically normal colonic mucosa: Biomarker for neoplasia risk. Gastroenterology 2008;135:1069-78. (20 pages).
Siegel MP, Kim YL, Roy HK, Wali RK, Backman V. Assessment of blood supply in superficial tissue by polarization-gated elastic light-scattering spectroscopy. Applied Optics 2006;45:335-42. (8 pages).
Turzhitsky VM, Gomes AJ, Kim YL, et al. Measuring mucosal blood supply in vivo with a polarization-gating probe. Applied Optics 2008;47:6046-57. (22 pages).
Gomes AJ, Ruderman S, DelaCruz M, Wali RK, Roy HK, Bachman V. In vivo measurement of the shape of the tissue-refractive-index correlation function and its application to detection of colorectal field carcinogenesis. Journal of Biomedical Optics 2012;17. (9 pages).
Roy HK, Gomes AJ, Ruderman S, et al. Optical Measurement of Rectal Microvasculature as an Adjunct to Flexible Sigmoidosocopy: Gender-Specific Implications. Cancer Prevention Research 2010;3:844-51. (9 pages).
Ruderman S, Mueller S, Gomes A, Rogers J, Backman V. Method of detecting tissue contact for fiber-optic probes to automate data acquisition without hardware modification. Biomedical Optics Express 2013;4:1401-12. (12 pages).
Ruderman S, Valuckaite V, Almoghrabi A, et al. Early Angiogenic Changes Associated With Field Carcinogenesis in Experimental Colon Cancer. Gastroenterology 2015; 148:S172-S, (1 page).
Valuckaite V, Ruderman S, Almoghrabi A, et al. A Novel Use of Angiotensin II Receptor Blocker (ARB) Losartan to Inhibit AOM Induced Tumorigenesis and Neoangiogenesis in Experimental Colon Cancer. Gastroenterology 2015;148:S172-S, (1 page).
Siegel MP, Kim YL, Roy HK, Wali RK, Backman V. Assessment of blood supply in superficial tissue by polarization-gated elastic light-scattering spectroscopy. Appl Opt 2006;45:335-42. (8 pages).
Roy HK, Wali RK, Kim Y, et al. Inducible nitric oxide synthase (iNOS) mediates the early increase of blood supply (EIBS) in colon carcinogenesis. FEBS Lett 2007;581:3857-62. (12 pages).
Roy HK, Turzhitsky V, Kim YL, et al. Spectral slope from the endoscopically-normal mucosa predicts concurrent colonic neoplasia: a pilot ex-vivo clinical study. Dis Colon Rectum 2008;51:1381-6. (11 pages).
Gomes AJ, Roy HK, Turzhitsky V, et al. Rectal mucosal microvascular blood supply increase is associated with colonic neoplasia. Clin Cancer Res 2009;15:3110-7. (9 pages).
Wallace MB, Gomes A, Roy HK, Backman V. Polarization Gating Spectroscopy of Normal Appearing Duodenal Mucosa to Detect Pancreas Cancer Gastrointestinal Endoscopy 2014:in press, (20 pages).
Yi J, Chen S, Backman V, Zhang HF. In vivo functional microangiography by visible-light optical coherence tomography. Biomedical Optics Express 2014;5:3603-12. (10 pages).
Yi J, Wei Q, Liu WZ, Backman V, Zhang HF. Visible-light optical coherence tomography for retinal oximetry. Optics Letters 2013;38:1796-8. (9 pages).
Yi J, Liu , Chen S, et al. Visible light optical coherence tomography measures retinal oxygen metabolic response to systemic oxygenation. Light Sci Appl 2015;4:e334. (22 pages).
Capoglu IR, Rogers JD, Ruiz CM, et al. FDTD and PSTD Applications in Biophotonics2013. (45 pages).
Myaing MT, MacDonald DJ, Li X. Fiber-optic scanning two-photon fluorescence endoscope. Optics Letters 2006;31:1076-8. (3 pages).
Roy HK, Turzhitsky V, Kim Y, et al. Association between Rectal Optical Signatures and Colonic Neoplasia: Potential Applications for Screening. Cancer Research 2009;69:4476-83. (17 pages).
Ruderman S, Gomes AJ, Stoyneva V, et al. Analysis of pressure, angle and temporal effects on tissue optical properties from polarization-gated spectroscopic probe measurements. Biomedical Optics Express 2010;1:489-99. (11 pages).
Gomes AJ, Backman V. Analytical light reflectance models for overlapping illumination and collection area geometries. Applied Optics 2012;51:8013-21. (19 pages).
Gomes AJ, Turzhitsky V, Ruderman S, Backman V. Monte Carlo model of the penetration depth for polarization gating spectroscopy: influence of illumination-collection geometry and sample optical properties. Applied Optics 2012;51:4627-37. (21 pages).

(56) References Cited

OTHER PUBLICATIONS

Gomes AJ, Backman V. Algorithm for automated selection of application-specific fiber-optic reflectance probes. Journal of Biomedical Optics 2013;18. (13 pages).
Gomes AJ, Wolfsen HC, Wallace MB, Cayer FK, Backman V. Monte Carlo model of the depolarization of backscattered linearly polarized light in the sub-diffusion regime. Optics Express 2014;22:5325-40. (16 pages).
Knudsen AB, Zauber AG, Rutter CM, et al. Estimation of Benefits, Burden, and Harms of Colorectal Cancer Screening Strategies: Modeling Study for the US Preventive Services Task Force. JAMA 2016;315:2595-609. (33 pages).
Schroy PC, 3rd, Coe A, Chen CA, O'Brien MJ, Heeren TC. Prevalence of advanced colorectal neoplasia in white and black patients undergoing screening colonoscopy in a safety-net hospital. Ann Intern Med 2013;159:13-20. (23 pages).
Lieberman DA, Rex DK, Winawer SJ, et al. Guidelines for colonoscopy surveillance after screening and polypectomy: a consensus update by the US Multi-Society Task Force on Colorectal Cancer. Gastroenterology 2012;143:844-57. (14 pages).
Brenner H, Hoffmeister M, Stegmaier C, Brenner G, Altenhofen L, Haug U. Risk of progression of advanced adenomas to colorectal cancer by age and sex: estimates based on 840,149 screening colonoscopies. Gut 2007;56:1585-9. (5 pages).
Rex DK, Helbig CC. High yields of small and flat adenomas with high-definition colonoscopes using either white light or narrow band imaging. Gastroenterology 2007;133:42-7. (6 pages).
Jemal A, Siegel R, Ward E, Hao Y, Xu J, Thun MJ. Cancer statistics, 2009. CA Cancer J Clin 2009;59:225-49. (25 pages).
Van Rijn JC, Reitsma JB, Stoker J, Bossuyt PM, van Deventer SJ, Dekker E. Polyp miss rate determined by tandem colonoscopy: a systematic review. Am J Gastroenterol 2006;101:343-50. (8 pages).
Barclay RL, Vicari JJ, Doughty AS, Johanson JF, Greenlaw RL. Colonoscopic withdrawal times and adenoma detection during screening colonoscopy. N Engl J Med 2006;355:2533-41. (9 pages).
Rex DK, Rabinovitz R. Variable interpretation of polyp size by using open forceps by experienced colonoscopists. Gastrointest Endosc 2014;79:402-7. (6 pages).
Mersha TB, Abebe T. Self-reported race/ethnicity in the age of genomic research: its potential impact on understanding health disparities. Hum Genomics 2015;9:1. (15 pages).
Maglietta R, Liuzzi VC, Cattaneo E, et al. Molecular pathways undergoing dramatic transcriptomic changes during tumor development in the human colon. BMC Cancer 2012;12:608. (16 pages).
Manna SK, Tanaka N, Krausz KW, et al. Biomarkers of coordinate metabolic reprogramming in colorectal tumors in mice and humans. Gastroenterology 2014;146:1313-24. (22 pages).
Xie G, Wang CZ, Yu C, et al. Metabonomic Profiling Reveals Cancer Chemopreventive Effects of American Ginseng on Colon Carcinogenesis in Apc(Min/+) Mice. J Proteome Res 2015;14:3336-47. (22 pages).
Backshall A, Alferez D, Teichert F, et al. Detection of metabolic alterations in non-tumor gastrointestinal tissue of the Apc(Min/+) mouse by (1)H MAS NMR spectroscopy. J Proteome Res 2009;8:1423-30. (8 pages).
Dotto GP. Multifocal epithelial tumors and field cancerization: stroma as a primary determinant. J Clin Invest 2014;124:1446-53. (8 pages).
Kaneko T, Okiji T, Kaneko R, Suda H, Nor JE. Gene expression analysis of immunostained endothelial cells isolated from formaldehyde-fixated paraffin embedded tumors using laser capture microdissection—a technical report. Microsc Res Tech 2009;72:908-12. (10 pages).
Kuai XY, Ji ZY, Zhang HJ. Mitochondrial uncoupling protein 2 expression in colon cancer and its clinical significance. World J Gastroenterol 2010;16:5773-8. (6 pages).
Ussakli CH, Ebaee A, Binkley J, et al. Mitochondria and tumor progression in ulcerative colitis. J Natl Cancer Inst 2013;105:1239-48. (10 pages).
Cruz MD, Wali RK, Bianchi LK, et al. Colonic mucosal Fatty Acid synthase as an early biomarker for colorectal neoplasia: modulation by obesity and gender. Cancer epidemiology, biomarkers & prevention : a publication of the American Association for Cancer Research, cosponsored by the American Society of Preventive Oncology 2014;23:2413-21. (16 pages).
Momi N HL, Wali RK, Zhang W, Chhaparia A, Weber CR, Cruz MD, Roy HK. Metabolic Axis in Early Colon Carcinogenesis and NSAIDs Resistance: Potential Role of Adipogenic Regulator PRDM16. Gastroenterology (AGA abstract) 2015;148:S-368. (1 page).
Chowdhury S, Ali M, Yamaguchi J, Liss AS, Sontheimer A, Thayer SP. DPYSL3 Regulates TFF2/SMAD4 Tumor Suppressor Signaling in Pancreatic Cancer. Pancreas 2015;44:1366-7. (2 pages).
Yamaguchi J, Mino-Kenudson M, Liss AS, et al. Loss of Trefoil Factor 2 From Pancreatic Duct Glands Promotes Formation of Intraductal Papillary Mucinous Neoplasms in Mice. Gastroenterology 2016;151:1232-+. (23 pages).
Antic D, Jovanovic MP, Fekete MD, Cokic V. Assessment of bone marrow microvessel density in chronic lymphocytic leukemia. Appl Immunohistochem Mol Morphol 2010;18:353-6. (2 pages).
Mahzouni P, Mohammadizadeh F, Mougouei K, Moghaddam NA, Chehrei A, Mesbah A. Determining the relationship between "microvessel density" and different grades of astrocytoma based on immunohistochemistry for "factor VIII-related antigen" (von Willebrand factor) expression in tumor microvessels. Indian J Pathol Microbiol 2010;53:605-10. (3 pages).
Vani J A Konda VB, Sarah Ruderman, Urszula Dougherty, John Hart, Mariano Gonzalez Haba Ruiz, Vesta Valuckaite, Anirudh Kulkarni, Alessandro Fichera, Irving Waxman, Marc Bissonnette. In vivo assessment of tumor vascularity using confocal laser endomicroscopy in murine models of colon cancer. Current Angiogenesis 2013;2:67-74. (1 page).
Du H, Shi H, Chen D, Zhou Y, Che G. Cross-talk between endothelial and tumor cells via basic fibroblast growth factor and vascular endothelial growth factor signaling promotes lung cancer growth and angiogenesis. Oncol Lett 2015;9:1089-94. (6 pages).
Bonuccelli G, Tsirigos A, Whitaker-Menezes D, et al. Ketones and lactate "fuel" tumor growth and metastasis: Evidence that epithelial cancer cells use oxidative mitochondrial metabolism. Cell Cycle 2010;9:3506-14. (9 pages).
Martinez-Outschoorn UE, Pestell RG, Howell A, et al. Energy transfer in "parasitic" cancer metabolism: mitochondria are the powerhouse and Achilles' heel of tumor cells. Cell Cycle 2011;10:4208-16. (9 pages).
Migneco G, Whitaker-Menezes D, Chiavarina B, et al. Glycolytic cancer associated fibroblasts promote breast cancer tumor growth, without a measurable increase in angiogenesis: evidence for stromal-epithelial metabolic coupling. Cell Cycle 2010;9:2412-22. (12 pages).
Arcucci A, Ruocco MR, Granato G, Sacco AM, Montagnani S. Cancer: An Oxidative Crosstalk between Solid Tumor Cells and Cancer Associated Fibroblasts. Biomed Res Int 2016;2016:4502846. (7 pages).
Georgakoudi I, Quinn KP. Optical imaging using endogenous contrast to assess metabolic state. Annu Rev Biomed Eng 2012;14:351-67. (19 pages).
Bhaskaran K, Douglas I, Evans S, van Staa T, Smeeth L. Angiotensin receptor blockers and risk of cancer: cohort study among people receiving antihypertensive drugs in UK General Practice Research Database. BMJ 2012;344:e2697. (16 pages).
Rosenberg DW, Giardina C, Tanaka T. Mouse models for the study of colon carcinogenesis. Carcinogenesis 2009;30:183-96. (14 pages).
Reddy BS. Studies with the azoxymethane-rat preclinical model for assessing colon tumor development and chemoprevention. Environ Mol Mutagen 2004;44:26-35. (10 pages).
Wali RK, Kunte DP, Koetsier JL, Bissonnette M, Roy HK. Polyethylene glycol-mediated colorectal cancer chemoprevention: roles of epidermal growth factor receptor and Snail. Mol Cancer Ther 2008;7:3103-11. (16 pages).
Fernandez-Fernandez FJ. Antineoplastic potential of metformin in colorectal cancer. Eur J Intern Med 2017;37:e22. (1 page).

(56) References Cited

OTHER PUBLICATIONS

Roy HK, Liu Y, Wali RK, et al. Four-dimensional elastic light-scattering fingerprints as preneoplastic markers in the rat model of colon carcinogenesis. Gastroenterology 2004;126:1071-81; discussion 948. (11 pages).
International Search Report and Written Opinion of International Searching Authority for Application No. PCT/US2019/035844, dated Aug. 19, 2019 (8 pages).

* cited by examiner

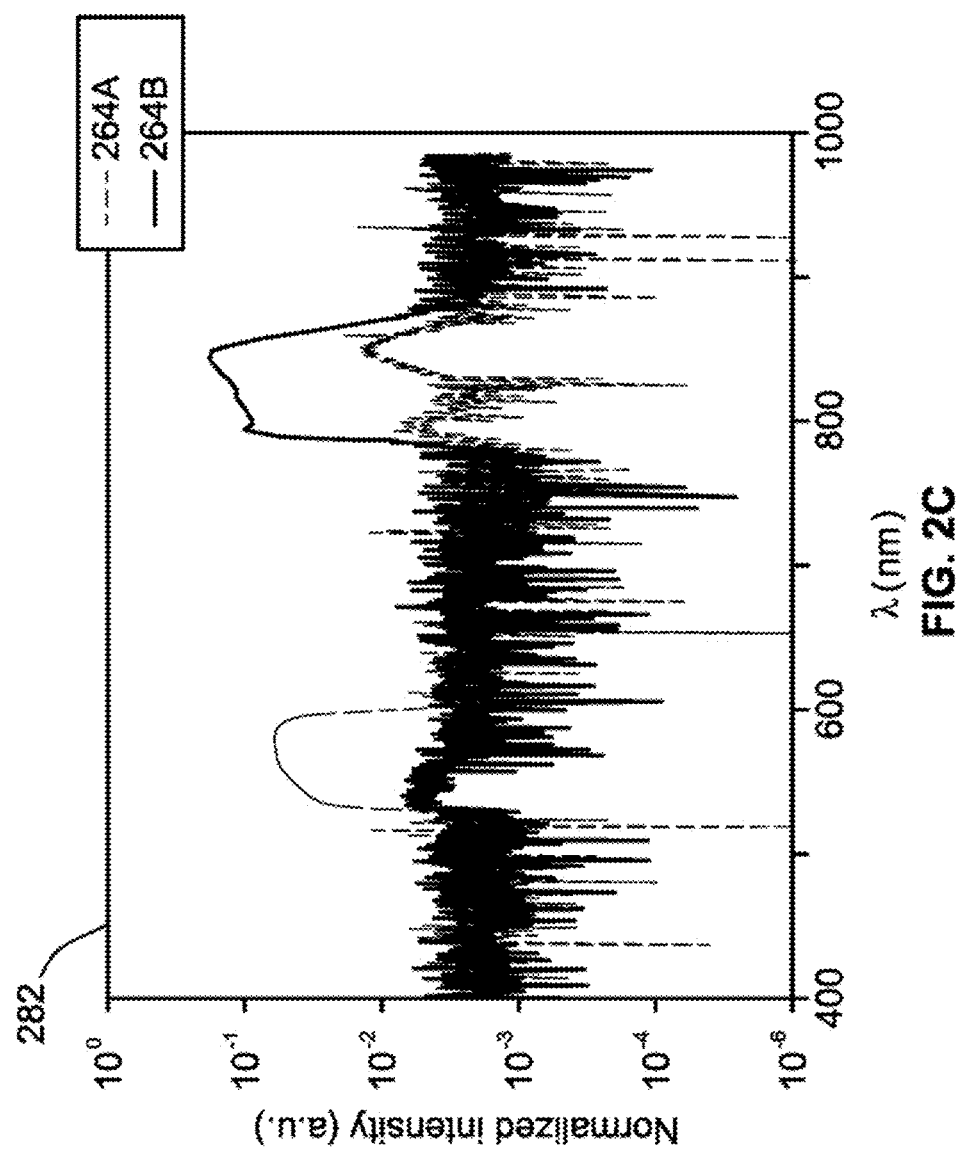

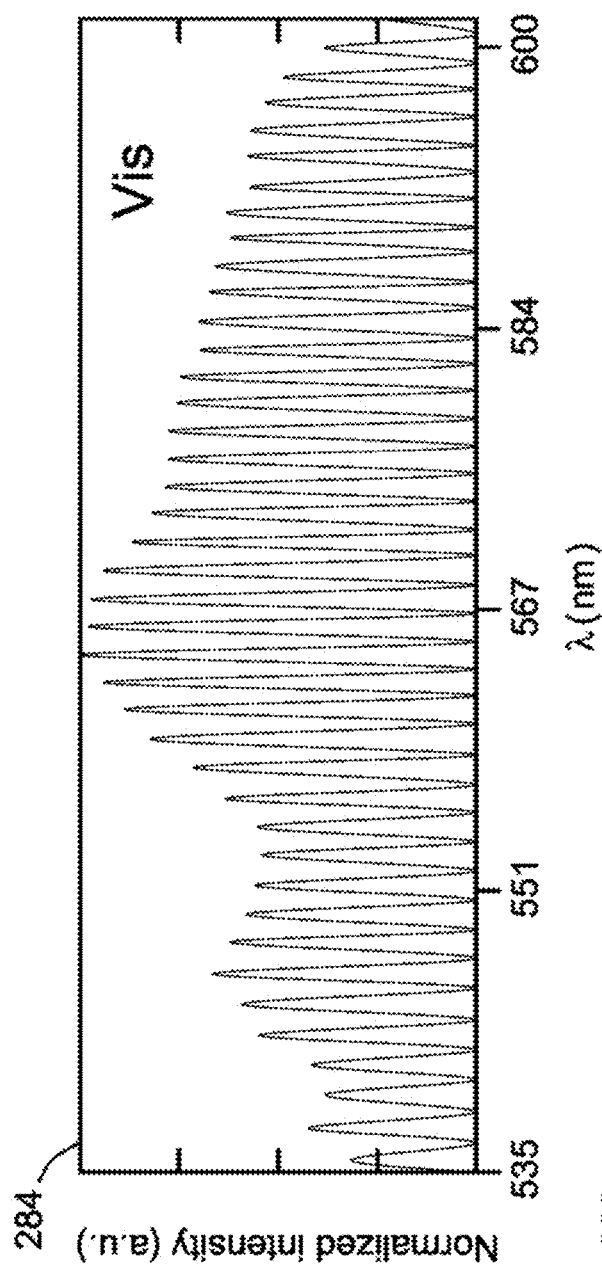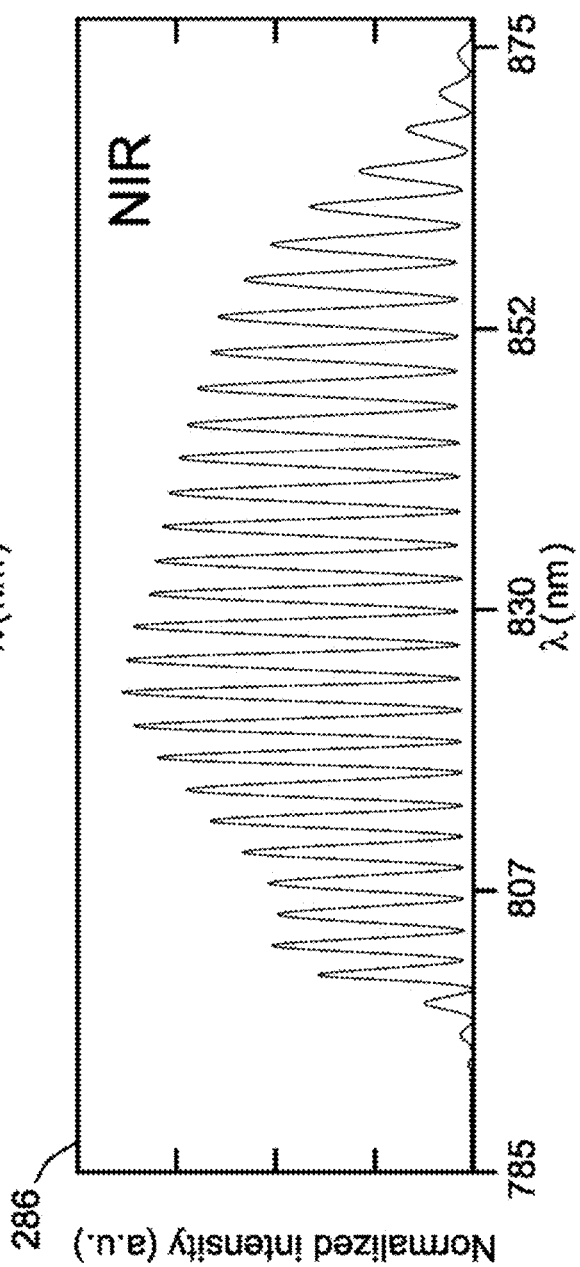
FIG. 2D
FIG. 2E

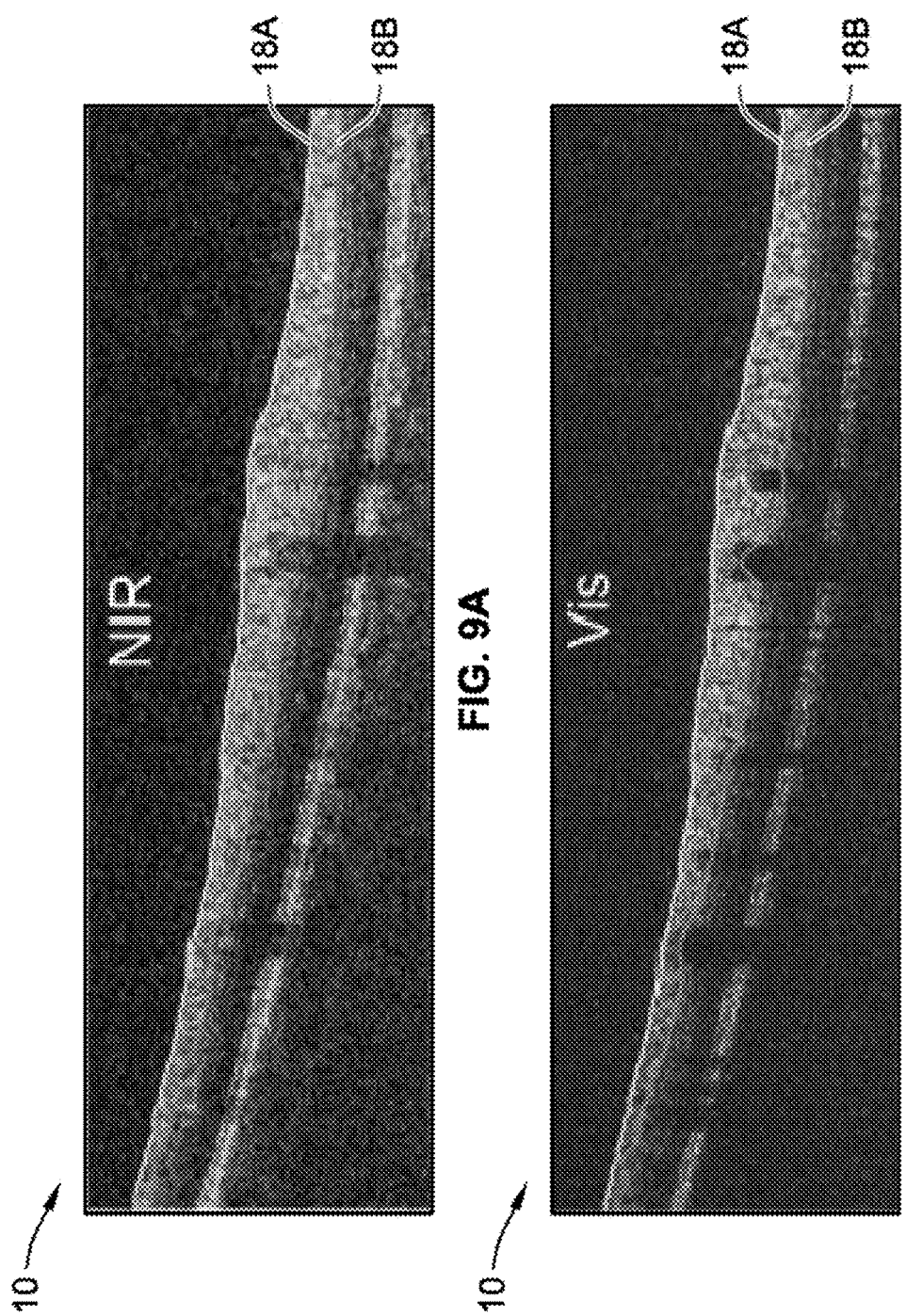

SYSTEMS AND METHODS FOR FIBER-BASED VISIBLE AND NEAR INFRARED OPTICAL COHERENCE TOMOGRAPHY

CROSS-REFERENCE TO RELATED APPLICATIONS

This application claims the benefit of and priority to U.S. Provisional Patent Application Ser. No. 62/681,471, filed on Jun. 6, 2018, entitled "FIBER-BASED AND NEAR INFRARED OPTICAL COHERENCE TOMOGRAPHY (vnOCT) ENABLES QUANTITATIVE ELASTIC LIGHT SCATTERING SPECTROSCOPY IN HUMAN RETINA," which is hereby incorporated by reference herein in its entirety.

TECHNICAL FIELD

The present disclosure relates to optical imaging systems. Specifically, the present disclosure relates to performing fiber-based optical coherence tomography with both visible light and near infrared light.

BACKGROUND

Elastic light scattering spectroscopy is a technique for analyzing tissue samples as a result of the interaction between electromagnetic radiation (such as light) and the tissue sample. Optical coherence tomography ("OCT") is one technique for performing elastic light scattering spectroscopy. OCT allows for resolution of structural aspects of a tissue sample. However, this technique can present limitations on depth penetration and depth resolution, as well as imaging speed. Aspects of the present disclosure provide a new optical imaging system and methods that solves this problem and other problems.

SUMMARY

According to aspects of the present disclosure, an optical system for analyzing a tissue system includes a first optical combining component, a second optical combining component, and an optical hub. The first optical combining component includes a first input port, a second input port, and an output port. The first input port is configured to receive a first type of electromagnetic radiation, and the second input port is configured to receive a second type of electromagnetic radiation. The output port is configured to emit electromagnetic radiation that includes the first type of electromagnetic radiation and the second type of electromagnetic radiation. The optical hub includes a first port, a second port, a third port, and a fourth port. The first receives the emitted electromagnetic radiation from the first optical combining component. A sample beam of electromagnetic radiation is emitted from the second port of the fiber coupler. The sample beam contains both the first type of electromagnetic radiation and the second type of electromagnetic radiation. The sample beam reflects off the initial surface of the tissue sample and/or structures within the tissue sample, and propagates back to the second port of the fiber coupler. A reference beam of electromagnetic radiation is emitted from the third port of the fiber coupler. The reference beam contains both the first type of electromagnetic radiation and the second type of electromagnetic radiation. The reference beam reflects off the reference mirror and propagates back to the third port of the fiber coupler. The fiber coupler combines the reflected sample beam and the reflected reference beam and emits the combined beam at the fourth port. An input of the second optical combining component is configured to receive the combined sample beam and reference beam. Electromagnetic radiation of the first type from both the sample beam and the reference beam is emitted by a first output of the second optical combining component and received by a first analysis device. Electromagnetic radiation of the second type from both the sample beam and the reference beam is emitted by a second output of the second optical combining component and received by a second analysis device.

According to aspects of the present disclosure, a method for analyzing a tissue sample comprises: combining a first type of electromagnetic radiation and a second type of electromagnetic radiation; directing a sample beam of electromagnetic radiation that includes the first type of electromagnetic radiation and the second type of electromagnetic radiation to the tissue sample such that the sample beam of electromagnetic radiation reflects off the tissue sample; directing a reference beam of electromagnetic radiation that includes the first type of electromagnetic radiation and the second type of electromagnetic radiation to a mirror such that the reference beam of electromagnetic radiation reflects off the tissue sample; combining the reflected sample beam and the reflected reference beam; directing the first type of electromagnetic radiation from both the reflected sample beam and the reflected reference beam to a first analysis device; and directing the second type of electromagnetic radiation from both the reflected sample beam and the reflected reference beam to a second analysis device.

These and other capabilities of the invention, along with the invention itself, will be more fully understood after a review of the following figures, detailed description, and claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure will be better understood from the following description of exemplary embodiments together with reference to the accompanying drawings.

FIG. 2C is a plot of the spectral outputs of a wavelength-division multiplexer of the system of FIG. 2A, according to some implementations of the present disclosure;

FIG. 2D is an interoferogram of visible electromagnetic radiation reflected off a tissue sample and off a reference mirror, according to some implementations of the present disclosure;

FIG. 2E is an interoferogram of near infrared electromagnetic radiation reflected off a tissue sample and off a reference mirror, according to some implementations of the present disclosure;

FIG. 9A is a cross-section of a retina obtained using near infrared electromagnetic radiation with the upper and lower boundaries of the nerve fiber layer of the retina marked, according to some implementations of the present disclosure;

FIG. 9B is a cross-section of the retina of FIG. 9A obtained using visible electromagnetic radiation with the upper and lower boundaries of the nerve fiber layer of the retina marked, according to some implementations of the present disclosure;

Figure 1:
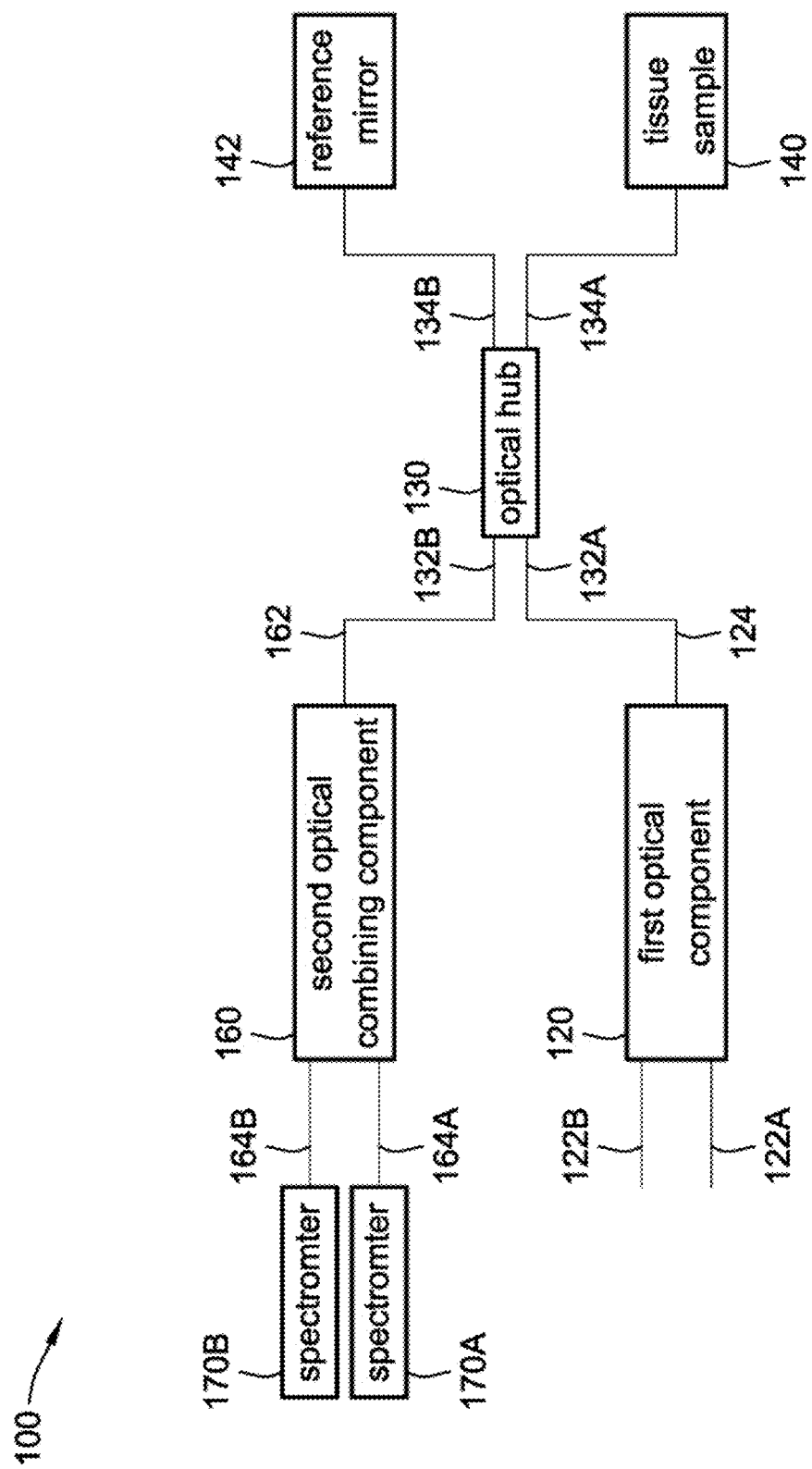
FIG. 1 is a block diagram of a system for using dual-band OCT to analyze a tissue sample, according to some implementations of the present disclosure.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation." Additionally, the singular terms "a," "an," and "the" include plural referents unless context clearly indicates otherwise.

The system of the present invention utilizes optical coherence tomography (OCT) techniques to obtain extra-dimensional images of tissue samples or objects within a tissue sample. OCT involves measuring electromagnetic radiation reflected off a tissue sample to obtain a 3D image of the tissue sample. Generally, an OCT system is divided into a reference path and a sample path. The sample path has the tissue sample to be imaged disposed at one end thereof. The reference path generally has a movable reference mirror disposed at the end thereof. In an exemplary setup, electromagnetic radiation is produced and is directed to a half-silvered mirror or other component that splits the electromagnetic radiation into two light rays traveling at 90° relative to each other. One light ray propagates down the reference path, strikes the reference mirror, and propagates back to the half-silvered mirror. The other light ray propagates down the sample path, strikes the tissue sample, and propagates back to the half-silvered mirror. There, the two light rays combine and propagate to a detector where they form an interference profile that is indicative of the different path lengths traveled by the electromagnetic radiation down the reference path and the sample path. As the distance between the half-silvered mirror and the reference mirror at the end of the reference path is known, this interference profile can be used to determine information about the distance traveled by the light ray reflected off of the tissue sample, and thus the structure of the tissue sample itself.

Some of the electromagnetic radiation that strikes the tissue sample will be reflected by an initial surface of the tissue sample, while some of the electromagnetic radiation will penetrate into the interior of the tissue sample and can reflect off of structures located at a depth within the tissue sample (e.g., located beneath or below the initial surface). The initial surface of the tissue sample is generally the outer surface of the tissue sample that is nearest to the electromagnetic radiation as it propagates from the half-silvered mirror. This depth is generally measured relative to the initial surface of the tissue sample which the electromagnetic radiation initially strikes. Generally, the electromagnetic radiation propagating in the sample path toward the tissue sample has a narrow spread such that the electromagnetic radiation is effectively concentrated at a single point on the initial surface of the tissue sample. By comparing the interference pattern produced by (i) electromagnetic radiation reflecting off the tissue sample or a structure within the tissue sample and (ii) electromagnetic radiation reflecting off the reference mirror, for a plurality of different positions of the reference mirror, the depth of the structure within the tissue sample can be determined. The electromagnetic radiation reflecting off the tissue sample can thus give information about structures located within the tissue sample that are generally in line with point on the initial surface of the tissue sample.

Interference profiles obtained from a beam of electromagnetic radiation concentrated at one point on the initial surface of the tissue sample thus gives a "depth profile" at that point. Cross-sectional images of the tissue sample, can be obtained by scanning the beam of electromagnetic radiation across the initial surface of the tissue sample in a first lateral direction. By then scanning the beam of electromagnetic radiation across the initial surface of the tissue sample in a second lateral direction orthogonal to the first lateral direction, a plurality of cross-sectional images are obtained that can be obtained to form a 3D image of the tissue sample, which shows structural details about portions of the tissue sample below the initial surface. OCT is thus able to provide 3D images of the tissue sample with a single scan across the 2D surface of the tissue sample without having to repeat the scan at a multiple different depth levels. OCT can also be used to perform an analysis of the tissue sample without actually producing a 2D or 3D image of the tissue sample.

OCT is generally capable of micron and sub-micron resolution, and can generally penetrate into a tissue sample a depth of up to approximately several millimeters. OCT is thus very sensitive to structural changes, even at sub-diffractional length scales (e.g. several tens of nanometers). OCT systems can also be used to measure blood flow, oxygenation, and capillary-level angiography, which make it a useful technique for viewing and characterizing biological tissue.

Systems and methods according to the present disclosure combine OCT performed with electromagnetic radiation in the visible wavelength range and OCT performed with electromagnetic radiation in the near-infrared wavelength range, known as dual-band OCT. Dual-band OCT can be used to produce 2D and 3D images of the tissue sample and structures within the tissue sample. The 2D and 3D images provide detail both about the structural properties of the tissue sample, and about molecular properties related to the absorption of the visible electromagnetic radiation and the near infrared electromagnetic radiation. Comparing data received from the two different wavelength ranges provides an extra dimension of analysis. Exemplary tissue samples that can be images by the systems and methods disclosed herein include human and animal retinas, human intestinal organoids (HIOs), and colon mucosa.

As used herein, "2D" means "two-dimensional" and "3D" means "three-dimensional."

As used herein, "electromagnetic radiation" refers to the output of a light source (e.g., including light in the visible and invisible spectrum), and may include electromagnetic waves or their quanta, photons, propagating at a variety of different predefined wavelengths and frequencies.

Referring now to FIG. 1, an embodiment of a system 100 for performing dual-band OCT to analyze a tissue sample 140 generally includes a first optical combining component 120, a second optical combining component 160, and an optical hub 130. The first optical combining component 120 has a first input port 122A, a second input port 122B, and an output 124. The first input port 122A receives a first type of electromagnetic radiation, while the second input port 122B receives a second type of electromagnetic radiation.

In some implementations, the two types of electromagnetic radiation are beams of electromagnetic radiation having one or more wavelengths in two different wavelength ranges. Because electromagnetic radiation is composed of individual photons each with its own wavelength, electromagnetic radiation in any given wavelength range will generally include one or more photons that each have a specific wavelength within that wavelength range. Thus, electromagnetic radiation will generally have one or more wavelengths within a certain wavelength range, which means that the electromagnetic radiation being referred to includes one or more photons that each have a wavelength in that wavelength range.

In some implementations, the first type of electromagnetic radiation is visible electromagnetic radiation, while the second type of electromagnetic radiation is near infrared electromagnetic radiation. The visible electromagnetic radiation could include the entire visible spectrum, or just a portion of the spectrum. Similarly, the near infrared electromagnetic radiation could include the entire near infrared spectrum, or just a portion of the near infrared spectrum. Generally, any suitable wavelength ranges can also be used in conjunction with the systems and methods described herein. For example, the two bands could be ultraviolet electromagnetic radiation and far infrared electromagnetic radiation. In other implementations, the two types of electromagnetic radiation have generally the same wavelength range, but have differences in other properties.

The first optical combining component 120 combines the two types of electromagnetic radiation into a single beam of electromagnetic radiation that is emitted at the output port 124. This single beam of electromagnetic radiation contains electromagnetic radiation of the first type (e.g., visible light) and electromagnetic radiation of the second type (e.g., near-infrared light).

The optical hub 130 includes a number of ports. Generally, electromagnetic radiation that is incident on one of the ports is emitted in some fashion by one or more of the other ports. The output port 124 of the first optical combining component 120 is optically coupled to a first port 132A of the optical hub 130, for example via an optical fiber or other optical components. The single beam of electromagnetic radiation emitted by the output port 124 of the first optical combining component 120 thus propagates to the first port 132A of the optical hub 130, and is then emitted by both a second port 134A of the optical hub 130 and a third port 134B of the optical hub 130. The electromagnetic radiation emitted by the second port 134A is directed toward the tissue sample 140, and is thus referred to as the sample beam of electromagnetic radiation. The electromagnetic radiation emitted by the third port 134B is directed toward a movable reference mirror 142, and is referred to as the reference beam of electromagnetic radiation. Both the sample beam of electromagnetic radiation and the reference beam of electromagnetic radiation contain both types of electromagnetic radiation (e.g., they both contain visible light and near-infrared light).

In some implementations, an optical fiber can carry the sample beam of electromagnetic radiation to the tissue sample 140. In other implementations, other components (which can include an optical fiber) can be used. For example, the system 100 may include a number of mirrors, telescopes, lenses, etc. in order to properly direct the sample beam of electromagnetic radiation to the tissue sample 140. Similarly, a number of optical components can carry the reference beam of electromagnetic radiation to the reference mirror 142. In still other implementations, the sample beam of electromagnetic radiation is sent to a probe that can be placed adjacent to or within the tissue sample 140 to be analyzed.

The sample beam of electromagnetic radiation reflects off the tissue sample 140 and propagates back to the second port 134A of the optical hub 130. Similarly, the reference beam of electromagnetic radiation reflects off the reference mirror 142 back to the third port 134B of the optical hub 130. The optical hub 130 combines the sample beam and the reference beam after they have reflected off the tissue sample 140 and the reference mirror 142, respectively. The combined sample beam and reference beam are emitted at a fourth port 132B of the optical hub 130.

The fourth port 132B of the optical hub 130 is optically coupled to an input port 162 of the second optical combining component 160. The second optical combining component 160 divides the combined sample and reference beams of electromagnetic radiation such that all of the electromagnetic radiation of the first type is emitted by a first output port 164A of the second optical combining component 160, and all of the electromagnetic radiation of a second type is emitted by a second output port 164B of the second optical combining component 160. Thus, the electromagnetic radiation emitted by the first output port 164A contains electromagnetic radiation of the first type from both the sample beam of electromagnetic radiation and the reference beam of electromagnetic radiation. Similarly, the electromagnetic radiation emitted by the second output port 164B contains electromagnetic radiation of the second type from both the sample beam of electromagnetic radiation and the reference beam of electromagnetic radiation.

The first output port 164A of the second optical combining component 160 is optically coupled to an analysis device 170A. In some implementations, the analysis device 170A is a spectrometer. The analysis device 170A could also be an imaging component such as a camera, photomultiplier tube array, etc. The analysis device 170A analyzes the electromagnetic radiation of the first type that reflected off the tissue sample 140 and off the reference mirror 142 to determine a property of the tissue sample 140. In some implementations, the first output port 164A of the second optical combining component 160 is coupled to the analysis device 170A via an optical fiber. The second output port 164B of the second optical combining component 160 is coupled to an analysis device 170B. Similar to analysis device 170A, analysis device 170B can be a spectrometer, a camera, a photomultiplier tube array, or any other suitable component for analyzing electromagnetic radiation. The analysis device 170B analyzes the electromagnetic radiation of the second type that reflected off the tissue sample 140 and the reference mirror 142 to determine a property of the tissue sample 140. In some implementations, only a single analysis device is used, and thus both the first output port 164A and the second output port 164B are coupled to the same analysis device.

In dual-band OCT, the electromagnetic radiation that reflects off the tissue sample 140 and the reference mirror 142 can be used to create 2D and 3D images of the tissue sample 140. After the first type of electromagnetic radiation from the sample beam and reference beam are combined, an interference pattern is created when the first type of electromagnetic radiation is incident on some surface or device, such as the analysis device 170A. Similarly, the second electromagnetic radiation from the sample beam and reference beam creates an interference pattern when it is incident on some surface or device, such as the analysis device 170B.

The interference pattern is indicative of the distance that was traveled by the first type of electromagnetic radiation in both the sample beam and the reference beam. The electromagnetic radiation from the two beams will generally interfere constructively if the difference in the distance that each traveled is equal to or less than the coherence length of the first type of electromagnetic radiation. If the distances traveled by the first type of electromagnetic radiation in the sample and reference beams differs by more than the coherence length, the two beam will interfere destructively. The analysis device can thus measure these interference patterns and the resulting intensity of the electromagnetic radiation that reaches the spectrometers.

When the sample beam of electromagnetic radiation is incident on the tissue sample 140, the electromagnetic radiation will generally reflect off some structure within the tissue sample 140. The depth of this structure within the tissue sample 140 determines the optical path length of the sample beam of electromagnetic radiation. Moving the reference mirror 142 back and forth adjusts the optical path length of the reference beam of electromagnetic radiation.

When the two optical path lengths are equal or within the coherence length of each other, the analysis devices 170A, 170B will measure a constructive interference pattern. Thus, by moving the reference mirror 142 back and forth and analyzing when a constructive interference pattern occurs and when a destructive interference pattern occurs, the system can determine how far into the tissue sample 140 the reflective structure is located. The data produced by the analysis devices 170A, 170B can be used for a variety of purposes, including creating 2D and 3D images of the tissue sample 140.

Figure 2A:
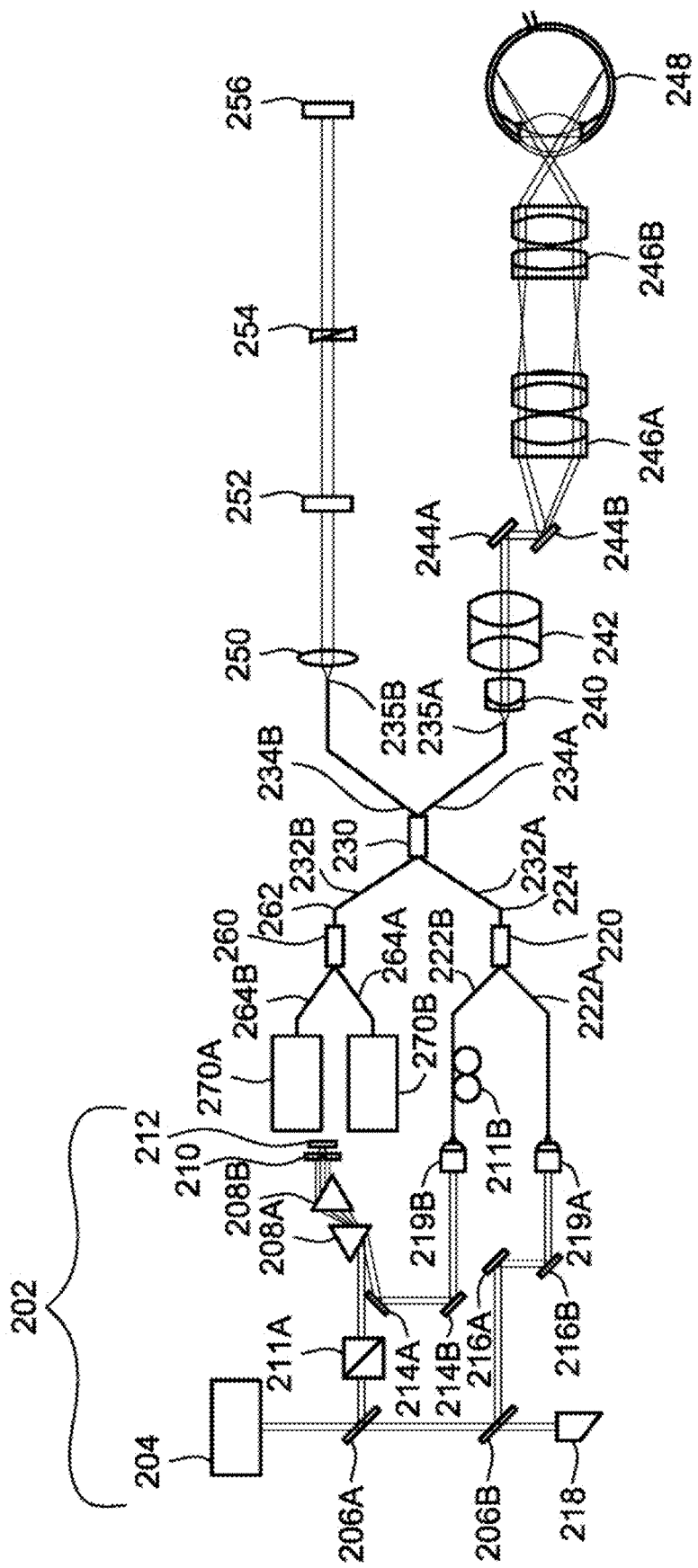
FIG. 2A is a system for using dual-band OCT with an achromatizing lens to analyze a tissue sample, according to some implementations of the present disclosure.

FIG. 2A shows another implementation of a system 200 for performing dual-band OCT on a tissue sample 248. System 200 is generally a more detailed version of system 100, and operates according to similar principles as system 100. The system 200 includes a first wavelength-division multiplexer 220 and a second wavelength-division multiplexer 260 that act as the first and second optical combining components. Both wavelength-division multiplexers are fiber-based. The optical hub is a 2×2 fiber coupler 230 with a 95:5 split ratio. Because the first and second wavelength-division multiplexers 220, 260 and the fiber coupler 230 are all fiber-based, all of (or a large portion of) the visible and near infrared electromagnetic radiation can generally propagate through the system in a single mode. The system 200 also includes spectrometers 270A and 270B that analyze the electromagnetic radiation that reflects off the tissue sample 248 and movable reference mirror 256.

The system 200 includes an initial stage 202 with any components necessary to send the first and second types of electromagnetic radiation to the first wavelength-division multiplexer 220. The initial stage 202 includes a broad-spectrum electromagnetic radiation source 204 that provides the different types of electromagnetic radiation. In one implementation, the first type of electromagnetic radiation is visible electromagnetic radiation in a wavelength range of between about 535 nanometers (nm) and about 600 nm, with a center wavelength of about 565 nm. The second type of electromagnetic radiation is near-infrared electromagnetic radiation in a wavelength range of between about 785 nm and about 875 nm, with a center wavelength of about 830 nm. In other implementations, the first type of electromagnetic radiation is visible electromagnetic radiation in a wavelength range of between about 520 nm and about 780 nm, and the second type of electromagnetic radiation is infrared or near infrared electromagnetic radiation in a wavelength range of between about 1200 nm and about 1300 nm. In still other implementations, the visible electromagnetic radiation is within a wavelength range of between about 380 nm and about 740 nm, and the near infrared electromagnetic radiation is within a wavelength range of between about 780 nm and about 2,500 nm.

Generally, the disclosure herein will refer to the two different types of electromagnetic radiation as visible electromagnetic radiation and near-infrared electromagnetic radiation. However, it is understood that electromagnetic radiation within generally any wavelength range can be used. Further, electromagnetic radiation that differs with respect to other properties can also be used as the different types of electromagnetic radiation.

The broad-spectrum electromagnetic radiation source 204 in system 200 produces electromagnetic radiation in a broad wavelength range that includes any wavelength necessary for performing dual-band OCT. Thus, in one implementation, the broad-spectrum electromagnetic radiation source 204 produces electromagnetic radiation that includes visible electromagnetic radiation and near-infrared electromagnetic radiation. In some implementations, the broad-spectrum electromagnetic radiation source 204 is a supercontinuum laser.

The initial stage 202 further includes a first dichroic mirror 206A and a second dichroic mirror 206B. Each dichroic mirror 206A, 206B reflects a certain wavelength range, while all other wavelength ranges transmit through the dichroic mirrors 206A, 206B. Dichroic mirror 206A is configured to reflect visible electromagnetic radiation and transmit all other electromagnetic radiation. In some implementation, dichroic mirror 206A has a cutting-off wavelength of about 650 nm. Electromagnetic radiation with a wavelength higher than the cutting-off wavelength (e.g., near infrared electromagnetic radiation) is transmitted through the dichroic mirror 206A, while electromagnetic radiation with a wavelength lower than the cutting-off wavelength (e.g., visible light) reflects off the dichroic mirror 206A.

In some implementations, the wavelength range of the visible electromagnetic radiation that reflects off the dichroic mirror 206A can be further narrowed using a pair of prisms 208A and 208B, a filter 210, and a mirror 212. For example, some visible electromagnetic radiation may be absorbed by certain tissue samples, and thus only a portion of the wavelength range of the electromagnetic radiation can be used to perform dual-band OCT (which relies on the incident electromagnetic radiation being reflected by the tissue sample 248). The prisms 208A, 208B disperse the visible electromagnetic radiation into discrete wavelength components. The discrete wavelength components then pass through the filter 210 that blocks the propagation of all of the visible electromagnetic radiation but for the desired wavelength range. The visible electromagnetic radiation in the desired wavelength range passes through the filter 210, reflects off the mirror 212, and propagates back through the pair of prisms 208A, 208B. After exiting the prisms 208A, 208B, mirrors 214A and 214B can be used to steer the visible electromagnetic radiation to the first wavelength-division multiplexer.

The electromagnetic radiation that passes through dichroic mirror 206A propagates to dichroic mirror 206B. Dichroic mirror 206B is configured such that electromagnetic radiation in the near infrared wavelength range reflects off dichroic mirror 206B and is directed to the first wavelength division multiplexer. Similar to the visible electromagnetic radiation, the near infrared electromagnetic radiation can be steered to the first wavelength-division multiplexer using mirrors 216A and 216B. The remaining electromagnetic radiation that is transmitted through dichroic mirror 206B is not used in the system 200, and can be directed to a beam trap 218 that absorbs the unused electromagnetic radiation. The beam trap 218 ensures that this unused electromagnetic radiation does not escape from the system and cause harm to people or other components.

The system 200 can also include a number of polarization components that ensure that the visible and near infrared electromagnetic radiation are appropriately polarized. In the illustrated implementation, the initial stage 202 includes a polarizing beam splitter 211A. The polarizing beam splitter 211A polarizes the visible electromagnetic radiation that reflects off dichroic mirror 206A so that only visible electromagnetic radiation of a single polarization passes through the prisms 208A and 208B. The initial stage can further include a polarization controller 211B that can adjust the polarization of the visible electromagnetic radiation before it enters the first wavelength-division multiplexer 220. The system 200 can include further or alternative polarization components in other locations within the system 200 to ensure the electromagnetic radiation is polarized as needed.

The first wavelength-division multiplexer 220 is a fiber-based component that mixes together the visible electromagnetic radiation and the near infrared electromagnetic radiation. As is shown in FIG. 2, the first wavelength-division multiplexer 220 has a first input port 222A that receives the visible electromagnetic radiation and a second input port 222B that receives the near infrared electromagnetic radiation. Collimating lenses 219A and 219B can be used to collimate the visible and near infrared electromagnetic radiation prior to being directed to the first and second input ports 222A, 222B of the first wavelength-division multiplexer 220. In the illustrated implementation of FIG. 2, collimating lenses 219A and 219B are coupled to the first and second input ports 222A and 222B, respectively, via optical fibers.

The mixed electromagnetic radiation (containing both visible electromagnetic radiation and near infrared electromagnetic radiation) is emitted from an output port 224 of the first wavelength-division multiplexer 220 and directed to the fiber coupler 230. The fiber coupler 230 generally includes a first set of ports that includes ports 232A and 232B, and a second set of ports that includes ports 234A and 234B. The output port 224 of the first wavelength-division multiplexer is optically coupled to port 232A of the fiber coupler 230 via an optical fiber. The fiber coupler 230 is a 2×2 fiber coupler, meaning that any electromagnetic radiation incident on either port 232A or 232B is emitted at port 234A and 234B. Similarly, any electromagnetic radiation that is incident on either port 234A or 234B is emitted at port 234A and 234B.

In some implementations, fiber coupler 230 has a 95:5 splitting ratio. The splitting ratio refers to how much of the electromagnetic radiation incident on one set of ports is emitted at each of port of the other set of ports, generally measured in the power of the emitted electromagnetic radiation. In system 200, 5% of the power of the electromagnetic radiation incident on port 232A from the first wavelength-division multiplexer 220 (which includes both visible and near infrared electromagnetic radiation) is emitted at port 234A, which leads to the tissue sample 248 The electromagnetic radiation emitted at port 234A towards the tissue sample 248 is referred to as the sample beam 235A of electromagnetic radiation. 95% of the power of the electromagnetic radiation incident on port 232A is emitted at port 234B, which leads to the movable reference mirror 256. The electromagnetic radiation emitted at port 234B towards the reference mirror 256 is referred to as the reference beam 235B of electromagnetic radiation. In other implementations, different splitting ratios can be used. For example, the fiber coupler 230 could have a splitting ratio of 90:10, or 50:50. Generally, any splitting ratio can be used as needed.

Because the tissue sample 248 can be an in vivo tissue sample (e.g., part of a living organism), the power of the sample beam 235A is generally limited so as to protect the tissue sample 248 and the organism from damage. In contrast, the power of the reference beam 235B does not need to be as limited, as the reference mirror 256 can reflect more powerful or intense electromagnetic radiation without being damaged. In some implementations, the power of the visible electromagnetic radiation in the sample beam 235A is about 0.2 milliwatts (mW), while the power of the near infrared electromagnetic radiation in the sample beam 235A is about 0.4 mW. These low power levels are generally used when the in vivo tissue sample 248 is a human retina. In these implementations, the power of the visible electromagnetic radiation in the reference beam 235B can be about 3.8 mW, while the power of the near infrared electromagnetic radiation in the reference beam 235B can be about 7.6 mW. Generally, when the tissue sample 248 is an in vivo tissue sample, the power of the any electromagnetic radiation incident on the tissue sample 248 is less than or equal to about 10.0 mW.

Generally, the power of the sample beam 235A and the reference beam 235B can be adjusted as needed by using different components in the system 200. For example, if more power is required for certain applications, a fiber coupler 230 with a different splitting ratio could be used, or a broad-spectrum electromagnetic radiation source 204 with a different output power could be used. Other components can also be placed into the path of the sample beam 235A, the reference beam 235B, or anywhere else in the system where electromagnetic radiation is propagating to attenuate the power of the electromagnetic radiation.

Figure 2B:
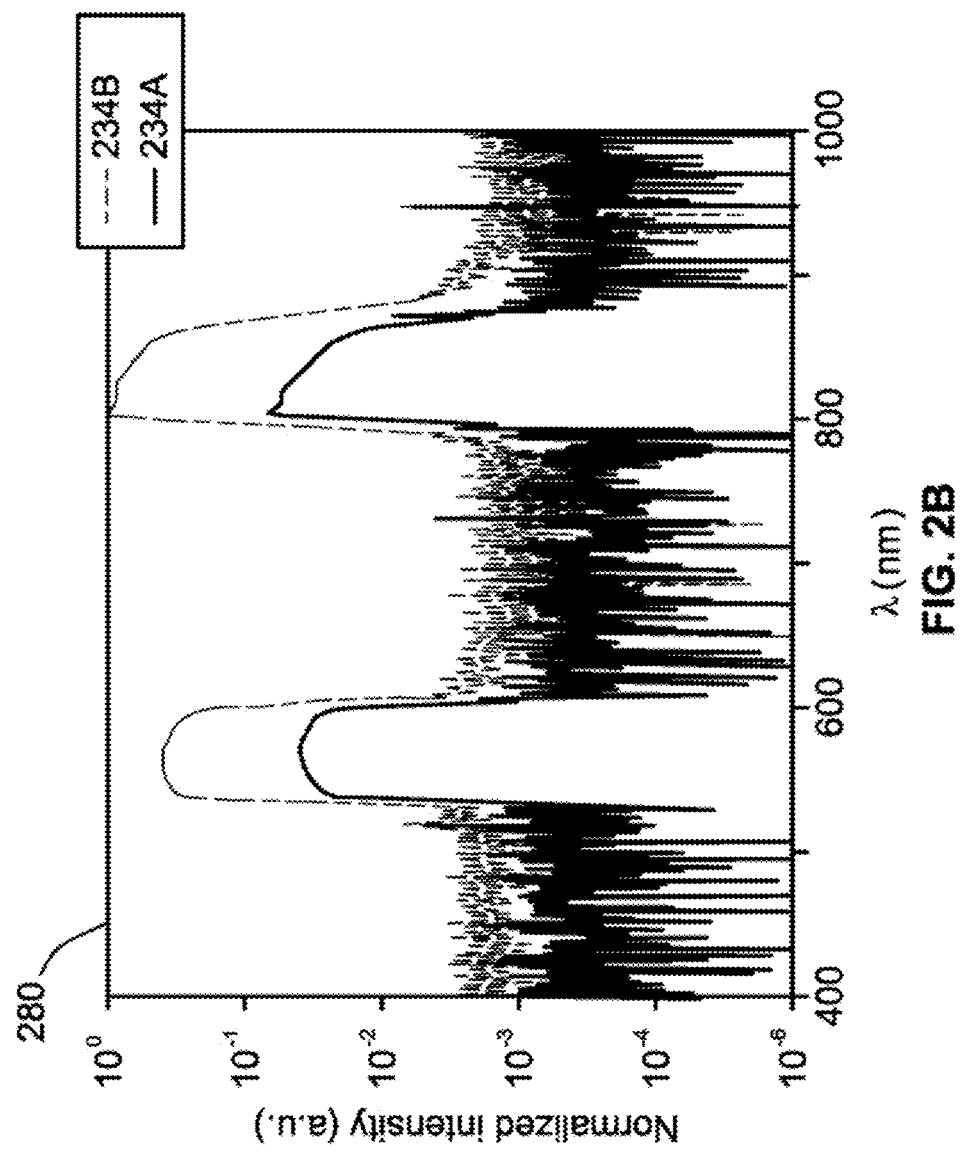
FIG. 2B is a plot of the spectral outputs of a fiber coupler of the system of FIG. 2A, according to some implementations of the present disclosure.

The sample beam 235A of electromagnetic radiation that is emitted at port 234A of the fiber coupler 230 contains both types of electromagnetic radiation, e.g., contains both visible electromagnetic radiation and near infrared electromagnetic radiation. Similarly, the reference beam 235B of electromagnetic radiation that is emitted at port 234B of the fiber coupler 230 contains visible electromagnetic radiation and near infrared electromagnetic radiation. FIG. 2B shows a spectral plot 280 of the output of ports 234A and 234B of the fiber coupler 230. The intensity of the electromagnetic radiation emitted at ports 234A and 234B (in arbitrary units) is plotted against the wavelength of the electromagnetic radiation in nanometers. The output at port 234A (which is the sample beam 235A) is shown with a thick solid line, while the output at port 234B (which is the reference beam 235B) is shown with a thinner dashed line.

As shown in the spectral plot 280, electromagnetic radiation in the sample beam 235A emitted at port 234A has spectral peaks in both the visible range (between about 535 nm and about 600 nm) and the near infrared range (between about 785 nm and about 875 nm). However, due to the 95:5 splitting ratio of the fiber coupler 230, the intensity/power of the reference beam 235B is over an order of magnitude higher than the intensity/power of the sample beam 235A.

Referring back to FIG. 2A, a number of optical components are used to steer and focus the sample beam 235A onto the tissue sample 248. These components include a collimating lens 240, an achromatizing lens 242, galvanometer mirrors 244A and 244B, and a 2:1 telescope system comprising lenses 246A and 246B. The collimating lens 240 collimates the sample beam 235A of electromagnetic radiation that is emitted from port 234A of the fiber coupler 230, and directs the sample beam 235A to the achromatizing lens 242.

The achromatizing lens 242 is generally used in system 200 when the tissue sample 248 is an eye. Generally, human eyes have significant chromatic aberration due to the dispersion of the water refractive index. The achromatizing lens is used to focus both the visible electromagnetic radiation and the near infrared electromagnetic radiation onto the eye. In some implementations, the achromatizing lens 242 is a triplet achromatizing lens with a center piece and two end pieces. After the sample beam 235A of electromagnetic radiation is focused by the achromatizing lens 242, it can be steered onto the tissue sample 248 by the pair of galvanometer mirrors 244A and 244B and the lenses 246A and 246B of the 2:1 telescope system. In some implementations, the diameter of the sample beam 235A of electromagnetic radiation as it strikes the tissue sample 248 is about 2 millimeters.

The mirrors 244A, 244B and lenses 246A, 246B can be used as needed for the design of the system 200. For example, implementations of system 200 other than the illustrated implementation may not require the use of mirrors 244A, 244B and lenses 246A, 246B to focus the sample beam 235A to the desired location on the tissue sample 248. Further, some implementations may require additional components beyond mirrors 244A, 244B and lenses 246A, 246B.

As the sample beam 235A of electromagnetic radiation strikes the tissue sample 248, the sample beam 235A will reflect off various structures that are located on the initial surface of the tissue sample 248 (which can be the outer surface of the tissue sample 248 that the electromagnetic radiation approaches first as it propagates from the fiber coupler 230) and/or within the interior of the tissue sample 248. After reflection, the electromagnetic radiation of the sample beam 235A propagates back through the various optical components to port 234A of the fiber coupler 230.

The system 200 also includes a number of optical components to steer the reference beam 235B of electromagnetic radiation to the reference mirror 256. In the illustrated implementation, these optical components include a collimating lens 250, a variable neutral density filter 252, and a dispersion compensator 254. The variable neutral density filter 252 is used to attenuate the power of the reference beam 235B of electromagnetic radiation. The attenuation ensures that that the OCT detection equipment (e.g., the spectrometers) is not oversaturated. The dispersion compensator 254 is used to compensate for any dispersion that may have been imparted to the reference beam 235B of electromagnetic radiation. In some implementations, the dispersion compensator 254 is made from one or more BK7 glass plates. After passing through the dispersion compensator 254, the reference beam 235B reflects off the reference mirror 256 and propagates back to port 234B of the fiber coupler 230. The reference mirror is generally mounted to some type of movable apparatus such as stepping motorized translation stage to allow the reference mirror 256 to be moved back and forth. This allows the optical path length of the reference beam 235B to be adjusted relative to the optical path length of the sample beam 235A.

After the sample beam 235A is reflected by the tissue sample 248 back to port 234A, and the reference beam 235B is reflected by the reference mirror 256 back to port 234B, the electromagnetic radiation from the sample beam 235A and the reference beam 235B is combined in the fiber coupler 230. Because the fiber coupler 230 is a 2:2 fiber coupler, the combined electromagnetic radiation is emitted at both port 232A and 232B. As noted above however, the splitting ratio of the fiber coupler 230 is 95:5. In the illustrated implementation of system 200, 95% of the power of the combined electromagnetic radiation from the sample beam 235A and reference beam 235B—after they have been reflected by the tissue sample 248 and the reference mirror 256 respectively—is emitted at port 232B of the fiber coupler 230. Only 5% of the power of the combined sample and reference beam 235B is emitted at port 232A.

Port 232B of the fiber coupler 230 is coupled to an input port 262 of the second wavelength-division multiplexer 260. The signal that is sent to the second wavelength-division multiplexer 260 thus includes visible electromagnetic radiation that reflected off the tissue sample 248 (from the sample beam 235A), visible electromagnetic radiation that reflected off the reference mirror 256 (from the reference beam 235B), near infrared electromagnetic radiation that reflected off the tissue sample 248 (from the sample beam 235A), and near infrared that reflected off the reference mirror 256 (from the reference beam 235B).

The second wavelength-division multiplexer 260 acts in a similar fashion as the first wavelength-division multiplexer 220, but in reverse. The second wavelength-division multiplexer 260 splits the electromagnetic radiation that is incident on input port 262 according to its wavelength. The second wavelength-division multiplexer 260 is designed so that all of the visible electromagnetic radiation that enters the input port 262 is emitted at a first output port 264A. All of the near infrared electromagnetic radiation that enters the input port 262 is emitted at a second output port 264B.

FIG. 2C shows a spectral plot 282 of the output of the first and second output ports 264A and 264B of the second wavelength-division multiplexer 260. The intensity of the electromagnetic radiation emitted at output ports 264A and 264B (in arbitrary units) is plotted against the wavelength of the electromagnetic radiation in nanometers. The spectrum of the output of the first output port 264A is shown with a thin dashed line, while the spectrum of the output of the second output port 264B is shown as a solid line. As is illustrated, the electromagnetic radiation emitted at the first output port 264A is primarily within a range of between about 535 nm and about 600 nm (corresponding to visible electromagnetic radiation). The spectral plot 282 in FIG. 2C shows that there is also a small amount of near infrared electromagnetic radiation emitted at the first output port 264A due to a small amount of inefficiency in the second wavelength-division multiplexer 260. However, a majority of the electromagnetic radiation emitted at the first output port 264A is visible electromagnetic radiation. Similarly, the electromagnetic radiation emitted at the second output port 264B is primarily within a range of between about 785 nm and about 875 nm (corresponding to near infrared electromagnetic radiation). A small portion of the electromagnetic radiation emitted at the second output port 264B is visible electromagnetic radiation.

Referring back to FIG. 2A, the first output port 264A of the second wavelength-division multiplexer 260 is optically coupled to the first spectrometer 270A, while the second output port 264B of the second wavelength-division multiplexer 260 is optically coupled to the second spectrometer 270B. The spectrometers 270A, 270B analyze the electromagnetic radiation that reflects off the tissue sample 248 and the reference mirror 256. The visible electromagnetic radiation from the sample beam 235A interferes with the visible electromagnetic radiation from the reference beam 235B when the visible electromagnetic radiation arrives at the spectrometer 270A. Similarly, the near infrared visible electromagnetic radiation from the sample beam 235A interferes with the near infrared electromagnetic radiation from the reference beam 235B when the near infrared electromagnetic radiation arrives at the spectrometer 270B. The resulting intensities of the visible and near infrared electromagnetic radiation are measured, and interferograms can be created. The intensities resulting from the interference is indicative of the optical path length difference between (i) the visible electromagnetic radiation that reflected off the tissue sample 248 and the visible electromagnetic radiation that reflected off the reference mirror 256, and (ii) the near infrared electromagnetic radiation that reflected off the tissue sample 248 and the near infrared electromagnetic radiation that reflected off the reference mirror 256. Thus, the intensities and optical path length differences provide information about where structures are located within the tissue sample 248. By moving the reference mirror 256, a plurality of intensity measurements can be made for the visible channel and the near infrared at multiple different depths within the tissue sample 248.

Based on these determinations, the spectrometers 270A, 270B can generate intensity measurements for both the visible and near infrared channels at the point on or within the tissue sample 248 being measured. By moving the reference mirror 256 back and forth, the spectrometers 270A, 270B can generate intensity measurements for a plurality of depths within the tissue sample 248.

Because the first wavelength-division multiplexer 220, the fiber coupler 230, and the second wavelength-division multiplexer 260 are all fiber-based components, it is understood that the various ports of these components are generally fibers that collect and carry electromagnetic radiation. For example, the first input port 222A of the first wavelength-division multiplexer 220 can be a fiber that is coupled to collimating lens 219A to collect the near infrared electromagnetic radiation. Similarly, the second input port 222B of the first wavelength-division multiplexer 220 can be a fiber that is coupled to collimating lens 219B to collect the visible electromagnetic radiation.

However, the various ports of the first wavelength-division multiplexer 220, the fiber coupler 230, and the second wavelength-division multiplexer 260 can also include other mechanism for receiving and emitting electromagnetic radiation. For example, the first and second input ports 222A, 222B of the first wavelength-division multiplexer 220 may collect the electromagnetic radiation from the collimating lenses 219A, 219B using suitable techniques or mechanism other than optical fibers.

Further, it is understood that in some implementations, the output port 224 of the first wavelength-division multiplexer 220 is generally coupled to port 232A of the fiber coupler 230, e.g., the output port 224 is one end of an optical fiber, while port 232A is the opposite end of the optical fiber.

FIG. 2D shows an example interferogram 284 produced by spectrometer 270A, while FIG. 2E shows an example interferogram 286 produced by spectrometer 270B. The interferogram 284 in FIG. 2D shows the interference pattern between the visible electromagnetic radiation that reflected off the tissue sample 248 and the reference mirror 256. Similarly, the interferogram 286 in FIG. 2E shows the interference pattern between the near infrared electromagnetic radiation that reflected off the tissue sample 248 and the near infrared electromagnetic radiation that reflected off the reference mirror 256. The interferograms 284, 286 are indicative of the relative intensity of the electromagnetic radiation from the sample beam 235A and the electromagnetic radiation from the reference beam 235B for a certain position of the reference mirror 256, which depends on the optical path length difference between the sample beam 235A and the reference beam 235B. The data produced by the spectrometers 270A and 270B can be used to create 2D and 3D images of the tissue sample 248, and perform other analyses. The data and images that are generated using visible electromagnetic radiation will generally be referred to as the "visible channel." Similarly, the data and images that are generated using near infrared electromagnetic radiation will generally be referred to as the "near infrared channel."

Figure 3A:
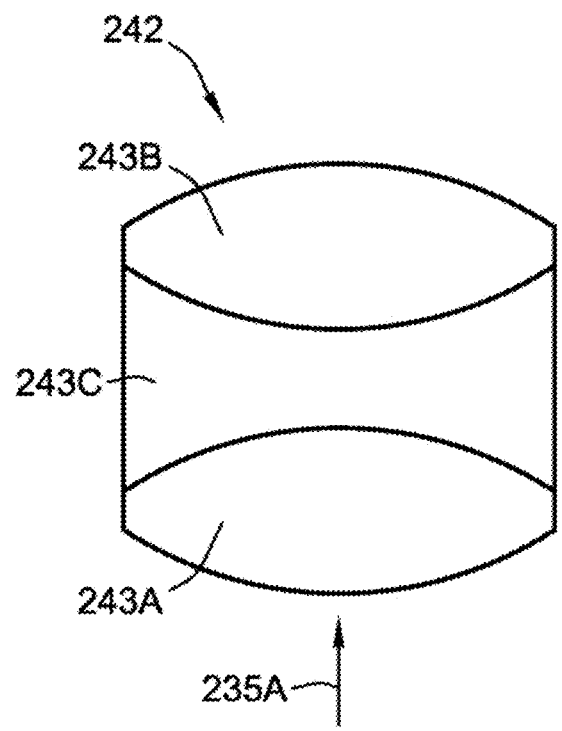
FIG. 3A is a perspective view of the achromatizing lens of the system of FIG. 2A, according to some implementations of the present disclosure.
Figure 3B:
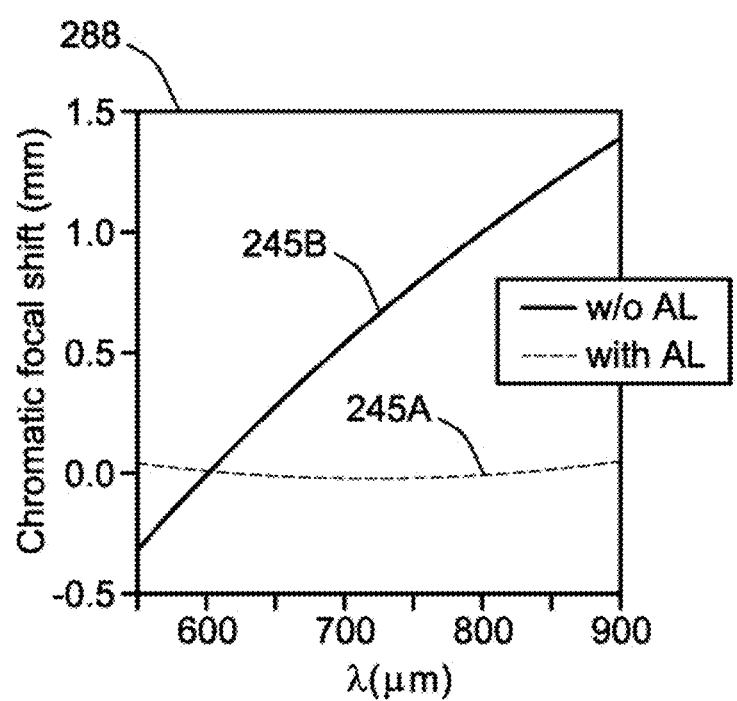
FIG. 3B is a plot of the chromatic focal shift of the system of FIG. 2A with and without the achromatizing lens of FIG. 3A, according to some implementations of the present disclosure.

FIG. 3A shows a side view of the achromatizing lens that is used to simultaneously focus both the visible electromagnetic radiation and the near infrared electromagnetic radiation on the tissue sample 248. The sample beam 235A of electromagnetic radiation is configured to propagate through the achromatizing lens 242 in the direction of the arrow. The achromatizing lens 242 is a triplet lens with a first end portion 243A, a second end portion 243B, and a central portion 243C. In some implementations, first and second end portions 243A and 243B are made of S-FPL53 optical glass, and the central portion 243C is made of H-ZF88 optical glass.

In the illustrated implementation, the first and second end portions 243A and 243B are both convex lens, and the central portion 243C is a concave lens. In some implementations, the radius of curvature of the convex lenses of both the first and second end portions 243A and 243B is between about 15.0 millimeters (mm) and about 25.0 mm, or between about 20.0 mm and about 23.0 mm. In one implementation, the radius of curvature of the convex lens of the first end portion 243A is about 22 mm, and the radius of curvature of the convex lens of the second end portion 243B is about 20 mm. In another implementation, the radius of curvature of the convex lens of the first end portion 243A is about 22.098 mm, and the radius of curvature of the convex lens of the second end portion 243B is about 20.043 mm.

The thickness of the widest portion of the convex lenses of the first and second end portions 243A and 243B can be between about 5.0 mm and about 15.0 mm, between about 10.0 mm and about 12.0 mm, or about 10.6 mm. The thickness of the thinnest portion of the concave lens of the central portion 243C can be between about 1.0 mm and about 10.0 mm, between about 2.0 mm and about 6.0 mm, less than about 5.0 mm, or about 4.0 mm. The transverse diameter of the achromatizing lens 242 (e.g., the thickness of the achromatizing lens 242 in a direction perpendicular to the arrow indicating the path of the sample beam 235A through the achromatizing lens 242) can be between about 15.0 mm and about 35.0 mm, between about 20.0 mm and about 30.00 mm, about 25.0 mm, or about 25.4 mm.

Figure 3C:
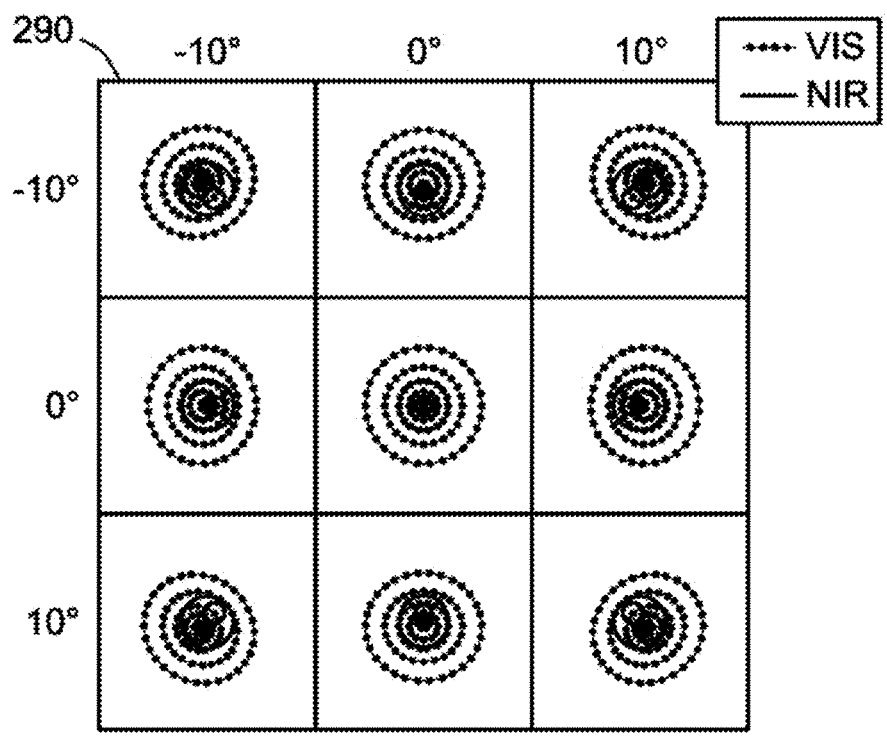
FIG. 3C is a spot diagram of the visible and near infrared channels of the system of FIG. 2A without the achromatizing lens of FIG. 3A, according to some implementations of the present disclosure.

The achromatizing lens 242 can simultaneously focuses both the visible electromagnetic radiation and the near infrared electromagnetic radiation onto the tissue sample 248 to correct the chromatic aberration of the tissue sample 248. FIG. 3C shows a plot 288 of the chromatic focal shift 245A between the visible and near infrared electromagnetic radiation in the sample beam 235A with the achromatizing lens 242, and the chromatic focal shift 245B between the visible and near infrared electromagnetic radiation in the sample beam 235A without the achromatizing lens 242. As shown, the chromatic focal shift 245A in the presence of the achromatizing lens 242 is negligible (or zero) for the range of wavelengths used in system 200. Without the achromatizing lens 242, the chromatic focal shift 245B is only zero for a very small wavelength range, and is significant for a large portion of the range of wavelengths used in system 200. In some implementations, the achromatizing lens 242 reduces the chromatic focal shift between the visible and near infrared electromagnetic radiation be about 40 micrometers.

Figure 3D:
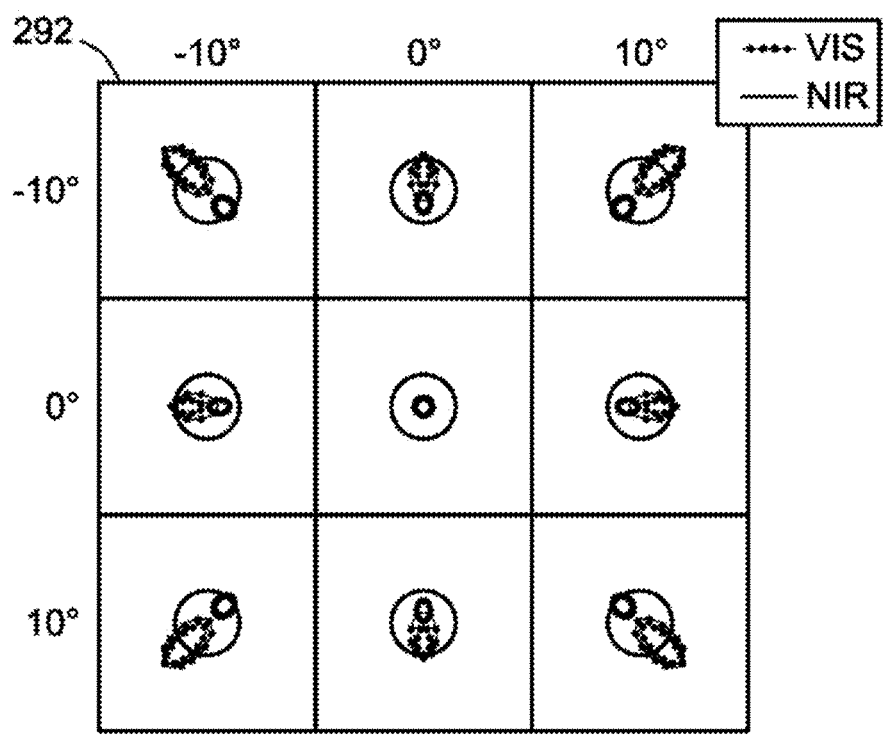
FIG. 3D is a spot diagram of the visible and near infrared channels of the system of FIG. 2A with the achromatizing lens of FIG. 3A, according to some implementations of the present disclosure.

FIG. 3D shows a spot diagram 290 of the system 200 during testing without the achromatizing lens 242. FIG. 3E shows a spot diagram 292 of the system 200 during testing with the achromatizing lens 242. In both spot diagrams 290 and 292, the spot that the visible electromagnetic radiation makes on the reference object (which could be the tissue sample 248 or a non-tissue object used for testing) is shown with a thin line with small circles, while the spot that the near infrared electromagnetic radiation makes on the reference object is shown with a thick line. Each spot diagram 290 and 292 contains nine different viewing angles. Both the horizontal viewing angle and the vertical viewing angle were set at either −10°, 0°, or 10°. As is demonstrated in the spot diagrams 290 and 292, the shift between the visible electromagnetic radiation and the near infrared electromagnetic radiation is much more significant without the achromatizing lens 242 (FIG. 3D) than it is with the achromatizing lens 242 (FIG. 3E).

Figure 4B:
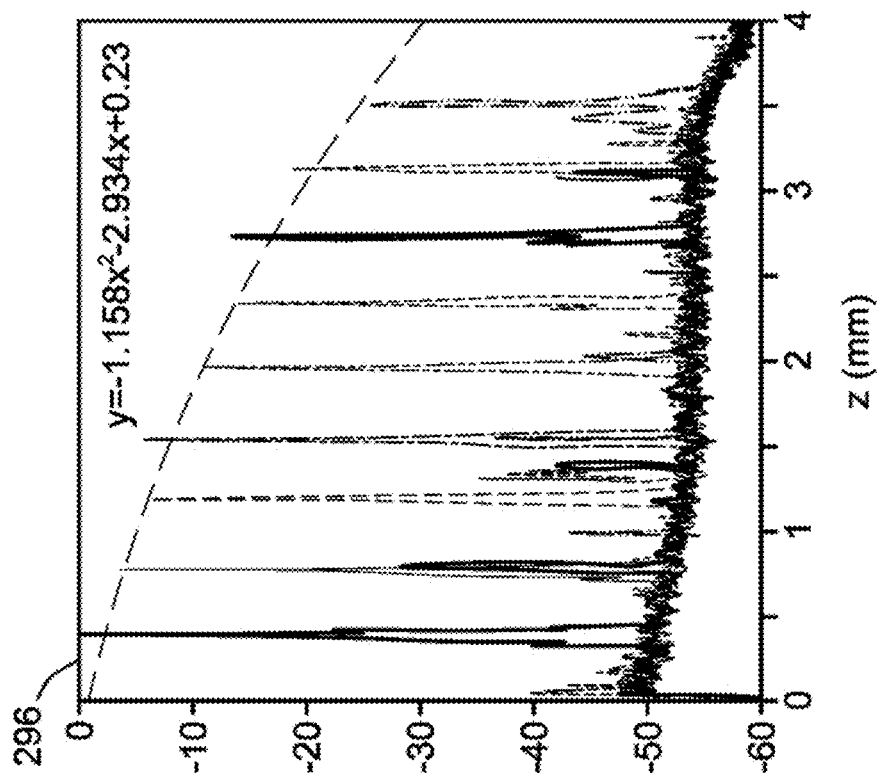
FIG. 4B is a plot of the roll-off performance of the system of FIG. 2A for the visible channel, according to some implementations of the present disclosure.
Figure 4A:
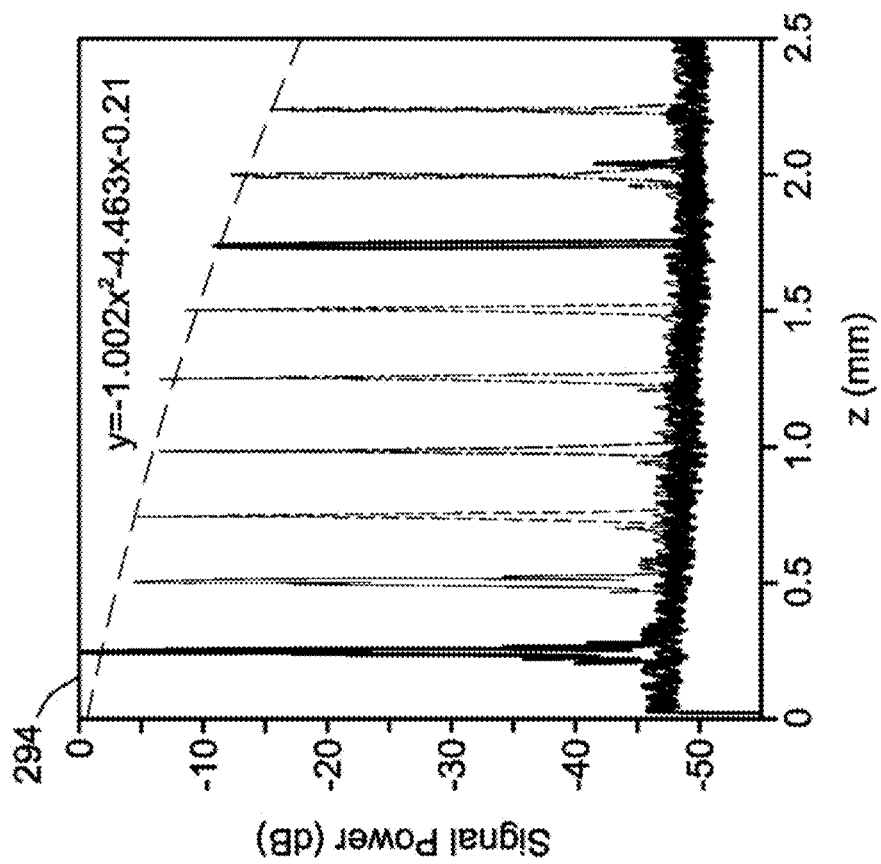
FIG. 4A is a plot of the roll-off performance of the system of FIG. 2A for the visible channel, according to some implementations of the present disclosure.

FIGS. 4A and 4B show roll-off curves of the system 200 for the visible electromagnetic radiation (FIG. 4A) and the near infrared electromagnetic radiation (FIG. 4B). FIG. 4A shows a plot 294 of the power of the reflected visible electromagnetic radiation measured in decibels (dB) against the penetration depth z in millimeters (measured relative to the initial surface of the tissue sample 248). FIG. 4B shows a plot 296 of the power of the reflected near infrared electromagnetic radiation measured in decibels (dB) against the penetration depth z in millimeters (measured relative to the initial surface of the tissue sample 248).

Generally, the tissue sample 248 will attenuate the incident electromagnetic radiation of the sample beam 235A as the electromagnetic radiation propagates into the tissue sample 248 and is reflected. This is referred to as the system roll-off. As shown by plots 294 and 296, portions of the sample beam 235A that reflect off structures deeper into the depth of the tissue sample 248 (e.g., further away from the initial surface of the tissue sample 248) are attenuated more than portions of the sample beam 235A that reflect off structures closer to the initial surface of the tissue sample 248.

However, the amount by which the visible and near infrared electromagnetic radiation are attenuated differ. As shown in FIG. 4B, the attenuation of the near infrared electromagnetic radiation at a given depth into the tissue sample 248 is greater than the attenuation of the visible near infrared at the same depth. Thus, measuring the same intensities with the spectrometers 270A, 270B may not indicate that the visible and near infrared electromagnetic radiation reflected off structures at the same depth within the tissue sample 248. To be able to correct for the system roll-off, the system 200 was tested and the roll-off curves in FIGS. 4A and 4B were generated. The roll-off curves were generated by incrementally measuring the power of the reflected signal at various depths into a reference object (which could be a tissue sample 248 or a non-tissue object used for testing). Curves were then fitted to the individual data peaks corresponding to each test. These curves can be used to correct the initial data obtained by the first and second spectrometers 270A and 270B.

Figure 5A:
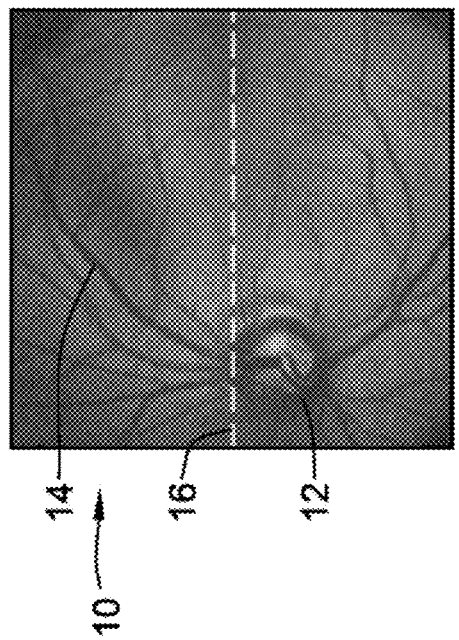
FIG. 5A is an en face projection of a retina obtained using visible electromagnetic radiation and a lens that focuses only near infrared electromagnetic radiation, according to some implementations of the present disclosure.
Figure 5B:
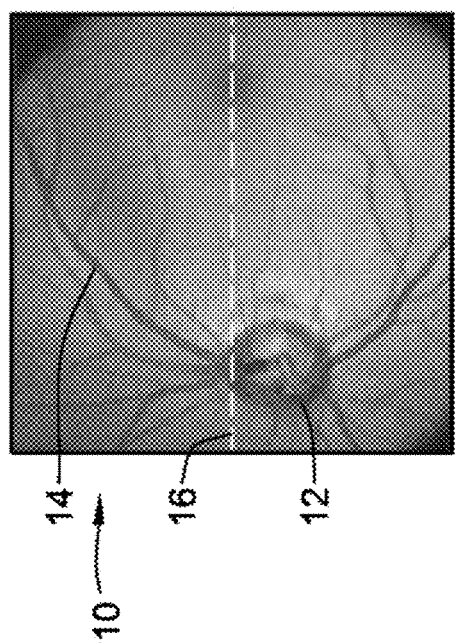
FIG. 5B is an en face projection of the retina of FIG. 5A obtained using near infrared electromagnetic radiation and the lens that focuses only near infrared electromagnetic radiation, according to some implementations of the present disclosure.

FIGS. 5A-5D show 2D and 3D images of a retina 10 that were obtained using the system 200 but without the achromatizing lens 242. Instead, the system 200 was set up to focus only the near infrared electromagnetic radiation. FIG. 5A shows an en face projection (e.g., generally forward looking) of the retina obtained using only visible electromagnetic radiation (which was not focused onto the retina), while FIG. 5B shows an en face of the retina obtained using only near infrared electromagnetic radiation (which was focused onto the retina). In both projections, the optic disc 12 and blood vessels 14 within the retina 10 are visible. As can be seen, the projection in FIG. 5A is darker and blurrier than the projection in FIG. 5B, as the visible electromagnetic radiation used for FIG. 5B was not focused onto the retina. In contrast, the projection in FIG. 5B is much clearer, as the visible electromagnetic radiation used was focused onto the retina. The optic disc 12 and blood vessels 14 in the projection in FIG. 5B are clearer as compared to the projection in 5A.

Figure 5C:
FIG. 5C is a cross-section of the retina of FIG. 5A obtained using visible electromagnetic radiation and the lens that focuses only near infrared electromagnetic radiation, according to some implementations of the present disclosure.
Figure 5D:
FIG. 5D is a cross-section of the retina of FIG. 5A obtained using near infrared electromagnetic radiation and the lens that focuses only near infrared electromagnetic radiation, according to some implementations of the present disclosure.

FIG. 5C shows a cross-section of the retina 10 at the location of the dashed reference line 16 in FIGS. 5A and 5B using only visible electromagnetic radiation. FIG. 5D shows a cross-section of the human retina at the location of the dashed lines in FIGS. 5A and 5B using only near infrared electromagnetic radiation. Similar to FIGS. 5A and 5B, the cross-section of FIG. 5D is generally clearer than the cross-section of FIG. 5C, because the near infrared electromagnetic radiation used in FIG. 5D was focused, while the visible electromagnetic radiation in FIG. 5C was not focused.

Figure 6A:
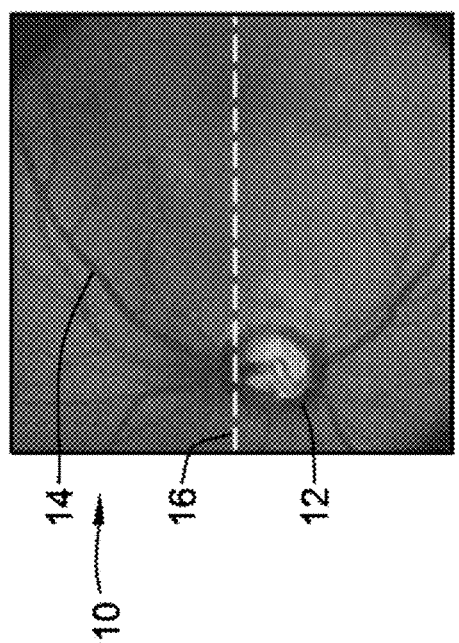
FIG. 6A is an en face projection of a retina obtained using visible electromagnetic radiation and a lens that focuses only visible electromagnetic radiation, according to some implementations of the present disclosure.
Figure 6B:
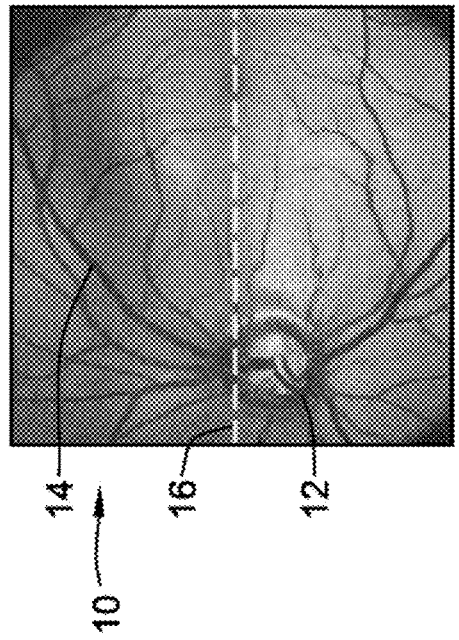
FIG. 6B is an en face projection of the retina of FIG. 6A obtained using near infrared electromagnetic radiation and the lens that focuses only visible electromagnetic radiation, according to some implementations of the present disclosure.

FIGS. 6A-6D show similar 2D and 3D images of the retina 10 as those of FIGS. 5A-5D, except that the system 200 was set up to focus only the visible electromagnetic radiation. FIG. 6A shows an en face projection of the retina obtained using only visible electromagnetic radiation (which was focused onto the retina), while FIG. 6B shows an en face projection of the retina obtained using only near infrared electromagnetic radiation (which was not focused onto the retina). As can be seen, the optic disc 12 and blood vessels 14 are clearer in the projection in FIG. 6A, where the electromagnetic radiation used was focused, as compared to the projection in FIG. 6B, wherein the electromagnetic radiation used was not focused.

Figure 6C:
FIG. 6C is a cross-section of the retina of FIG. 6A obtained using visible electromagnetic radiation and the lens that focuses only visible electromagnetic radiation, according to some implementations of the present disclosure.
Figure 6D:
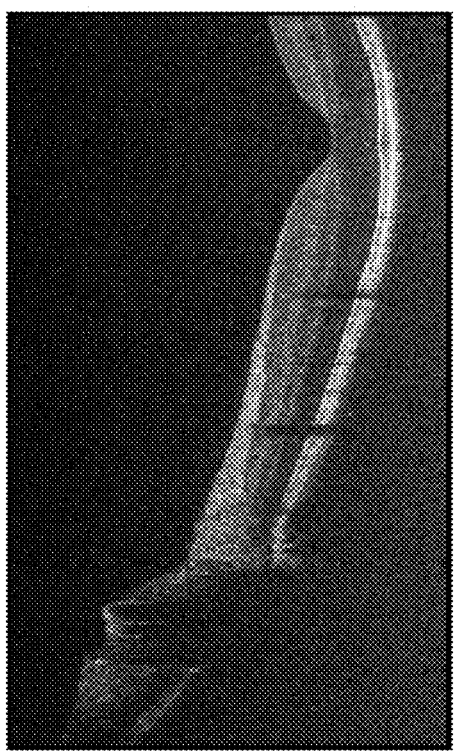
FIG. 6D is a cross-section of the retina of FIG. 6A obtained using near infrared electromagnetic radiation and the lens that focuses only visible electromagnetic radiation, according to some implementations of the present disclosure.

FIG. 6C shows a cross-section of the retina 10 at the location of the dashed reference lines 16 in FIGS. 6A and 6B using only visible electromagnetic radiation. FIG. 6D shows a cross-section of the human retina at the location of the dashed lines in FIGS. 6A and 6B using only near infrared electromagnetic radiation. Similar to FIGS. 6A and 6B, the cross-section of FIG. 6C is generally clearer than the cross-section of FIG. 6D.

Figure 7B:
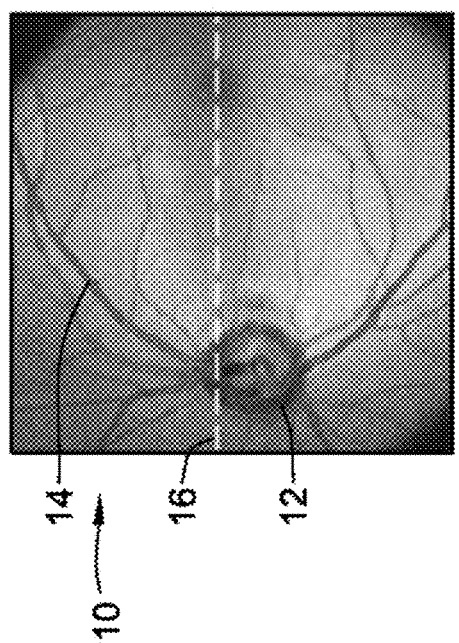
FIG. 7B is an en face projection of the retina of FIG. 7A obtained using near infrared electromagnetic radiation and the achromatizing lens of FIG. 3A, according to some implementations of the present disclosure.
Figure 7D:
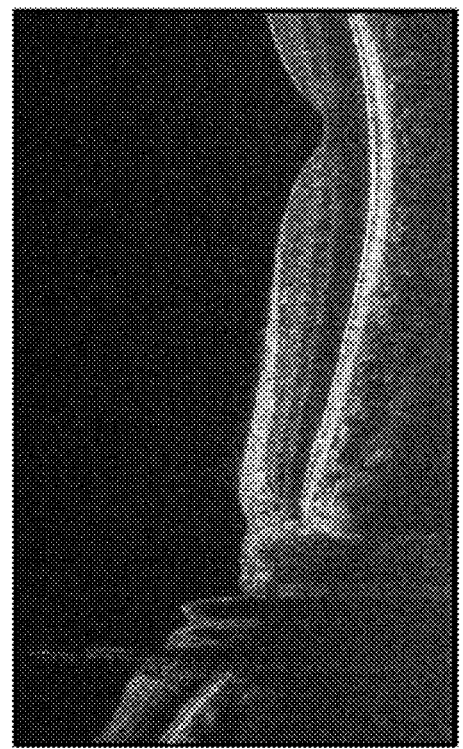
FIG. 7D is a cross-section of the retina of FIG. 7A obtained using near infrared electromagnetic radiation and the achromatizing lens of FIG. 3A, according to some implementations of the present disclosure.
Figure 7A:
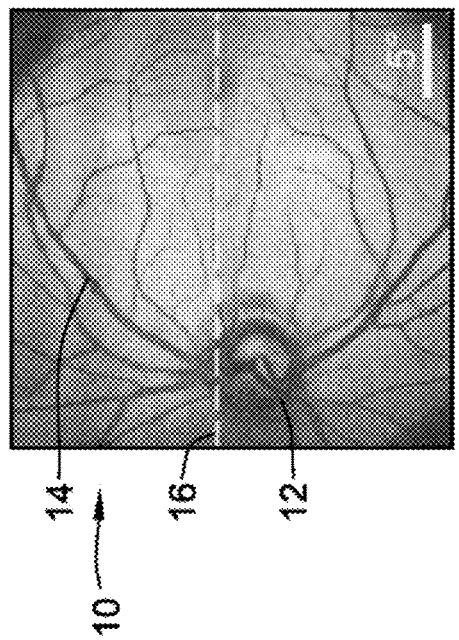
FIG. 7A is an en face projection of a retina obtained using visible electromagnetic radiation and the achromatizing lens of FIG. 3A, according to some implementations of the present disclosure.
Figure 7C:
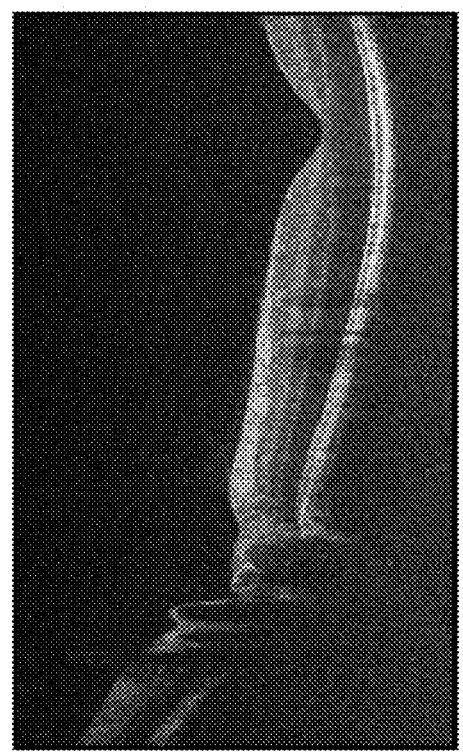
FIG. 7C is a cross-section of the retina of FIG. 7A obtained using visible electromagnetic radiation and the achromatizing lens of FIG. 3A, according to some implementations of the present disclosure.

FIGS. 7A-7D show similar 2D and 3D images of the retina 10 as FIGS. 5A-6D, except the achromatizing lens 242 was used. This allows both the visible and the near infrared electromagnetic radiation to be focused onto the retina. As a result, the images obtained using only visible electromagnetic radiation (FIGS. 7A and 7C) are generally in focus just as much as the images obtained using only near infrared electromagnetic radiation (FIGS. 7B and 7D). The optic disc 12 and the blood vessels 14 are clearly visible in both projections in FIGS. 7A and 7B.

Figure 8A:
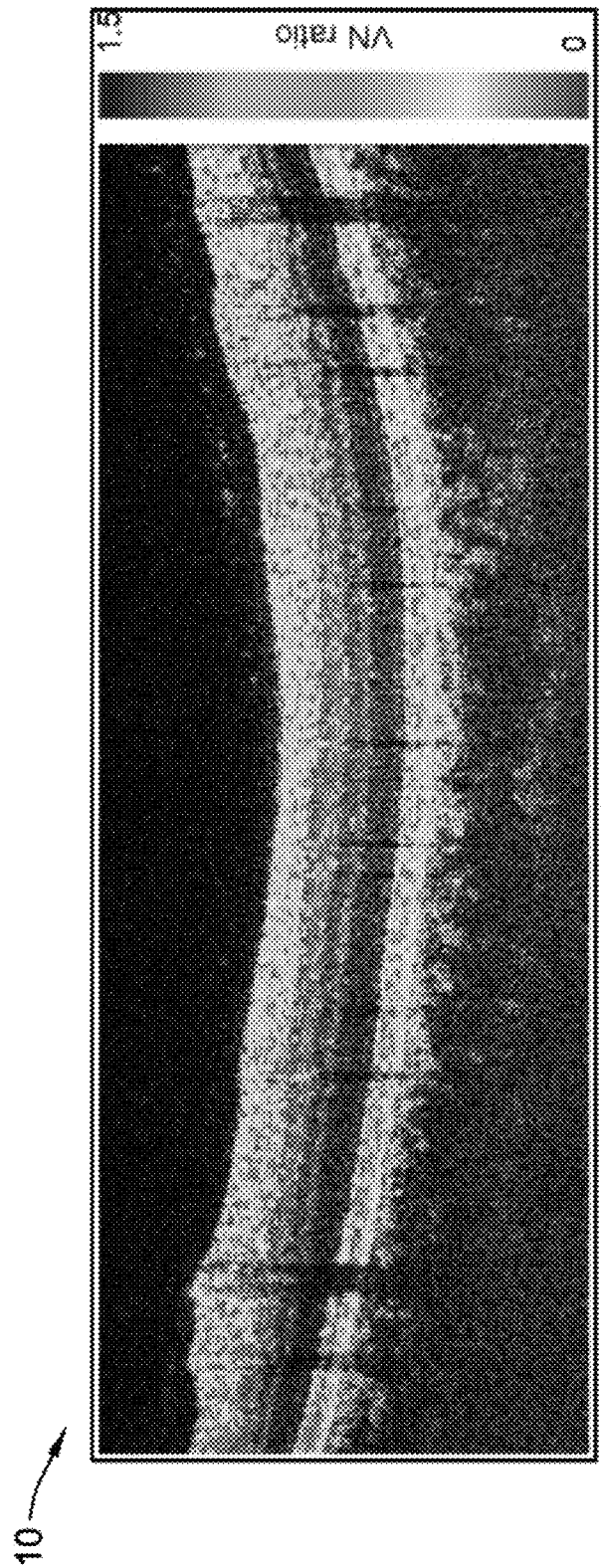
FIG. 8A is a cross-section of a retina obtained using both visible electromagnetic radiation and near infrared electromagnetic radiation, according to some implementations of the present disclosure.

FIG. 8A shows a combined cross-section image of a retina 10 obtained using both the visible electromagnetic radiation and the near infrared electromagnetic radiation. In this cross-section, data from both spectrometers 270A and 270B is used to illustrate an additional dimension, namely the comparison of the data from the visible electromagnetic radiation and the near infrared electromagnetic radiation. The cross-section in FIG. 8A shows the general structure of the retina 10 along the cross-section. However, the intensities of the resulting interference patterns for both the visible electromagnetic radiation and the near infrared electromagnetic radiation, for each pixel, were compared. The pixels can then be color-coded according to the ratio of these intensities to provide an additional dimension of information about the retina 10.

This ratio, referred to as the VN ratio, can provide details beyond the general shape of any structures in the retina. For example, different structures in the retina may reflect visible electromagnetic radiation differently than near infrared electromagnetic radiation, depending on the composition of the structure. While the interference pattern of either the visible electromagnetic radiation or the near infrared electromagnetic radiation may provide details on the shape of the structure, comparing the interference patterns can provide details about the composition of the structure. Generally, a cross-sectional image of a healthy retina can be expected to have a certain value of the VN ratio for every pixel. By comparing the VN ratios in a cross-sectional image of a retina being examined and comparing those to the expected VN ratios, additional information about the retina being imaged can be obtained. As shown in the scale to the right of image in FIG. 8A, in some implementations, the VN ratio is generally between about 0 and about 1.5.

Figure 8B:
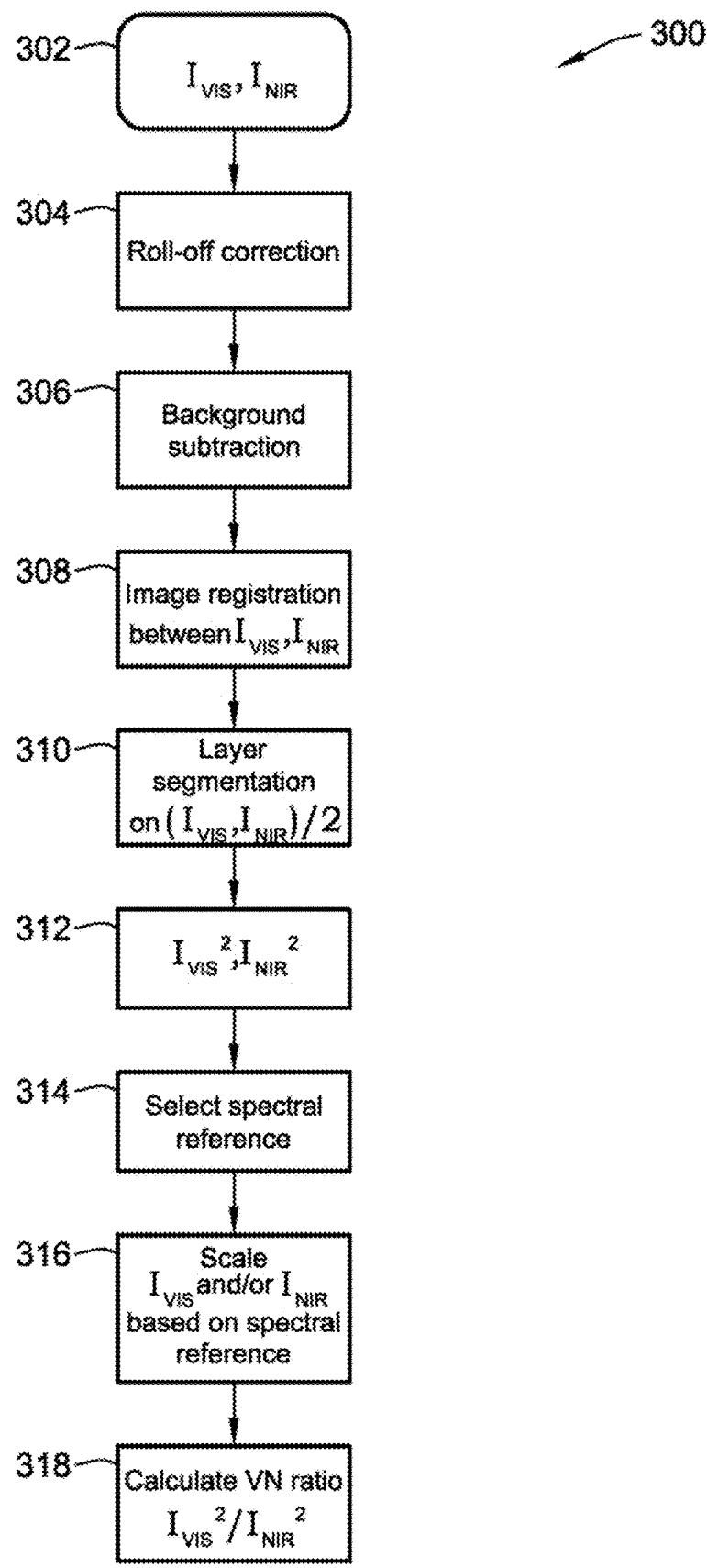
FIG. 8B is a method for performing dual-band OCT with visible electromagnetic radiation and near infrared electromagnetic radiation to obtain the cross-section of FIG. 8A, according to some implementations of the present disclosure.

FIG. 8B shows a method 300 for combining the data obtained using the visible electromagnetic radiation and the data obtained using the near infrared electromagnetic radiation to obtain the combined cross-section shown in FIG. 8A. At step 302, the initial data from spectrometers 270A and 270B is provided. This data is general referred to as $I_{VIS}$ and $I_{NIR}$, and is the resulting intensity of the interference pattern of both the visible electromagnetic radiation and the near infrared electromagnetic radiation for every point on the tissue sample that was measured. In the context of method 300, $I_{VIS}$ and $I_{NIR}$ generally refers to the intensity of each voxel of the images from the visible channel and from the near infrared channel. At step 304, roll-off correction is performed to correct for the system roll-off illustrated in FIGS. 4A and 4B.

As discussed herein with respect to FIGS. 4A and 4B, the visible electromagnetic radiation and the near infrared electromagnetic radiation reflected off the tissue sample 248 are attenuated at different rates. Because of this wavelength-specific attenuation, the depth indicated by the visible electromagnetic radiation in the reflected sample beam 235A may be different than the depth indicated by the near infrared electromagnetic radiation in the reflected sample beam 235A, even if both types of electromagnetic radiation reflected off the same structure within the tissue sample 248. The resulting images from the visible channel and the near infrared channel will be slightly offset due to the attenuation. This physical offset is calculated for all images (taking into account the refractive index of the tissue sample 248), and the images from one or both of the visible channel and the near infrared channel are corrected. At step 306, the background noise in the images is calculated based on the average intensity, and then subtracted. Next at step 308, the images from the visible channel and the near infrared channel are registered.

In order to obtain a combined cross-sectional image such as the image in FIG. 8A for a layer at a specific depth below the initial surface of the tissue sample 248, layer segmentation must be performed to identify different layers within the tissue sample 248. The layer segmentation is performed at step 310 in FIG. 8B. At step 310, the mean intensity $(I_{VIS}+I_{NIR})/2$ of the voxels is calculated. A moving average filter is then applied to smooth out the voxels and enhance the visibility of the boundary between layers. Next, an intensity threshold is set or calculated that indicates the edge of a layer. The intensities of the voxels at the edge of a given layer is generally different than the intensities of the voxels within the layer, and thus the intensity threshold is used to indicate where the edge of a given layer is.

In some implementations the intensity threshold is a lower threshold, and intensities above the threshold indicate the edge of the layer. In other implementations, the intensity threshold is an upper threshold, and intensities below the threshold indicate the edge of the layer. The intensity threshold could be a minimum intensity or a maximum intensity that the system 200 is configured to detect. In still other implementations, the intensity threshold is an intensity that is higher or lower than some reference intensity. In additional implementations, the intensity threshold is relative to the intensity of the immediately preceding or subsequent portion of the tissue sample that has been imaged. In general, the intensity threshold that is set is specific to the application that the system 200 is being used for.

The intensity threshold can be a minimum intensity to indicate a layer edge, or a maximum intensity to indicate a layer edge. In one implementation, the intensity threshold is calculated based on Otsu's method. Other methods of calculating or setting the intensity threshold can also be used. After the intensity threshold is set or calculated, the images from the visible and near infrared channels can binarized based on the intensity threshold to detect the layer. This process in step 310 can be repeated as many times as necessary depending on how many different layers there are in the tissue sample 248.

Generally, the first layer within the tissue sample 248 that is identified in step 310 is the outer surface of the tissue sample 248. This is the layer of the tissue sample 248 that the sample beam 235A strikes first. After the outer surface of the tissue sample 248 has been identified within the images from the visible and near infrared channels, additional layers within the tissue sample 248 can be identified. In one example, if the tissue sample 248 is a retina, the layers past the outer surface that can be identified can include the neural fiber layer, the inner and outer segment junctions, and the Bruch's membrane.

At step 312, the intensities from the visible channel and the near infrared channel are squared to ensure appropriate visibility in the combined cross-sectional image. At steps 314 and 316, systematic variations between the visible channel and the near infrared channel are eliminated using a spectral reference. At step 314, the spectral reference is selected. In some implementations, the spectral reference may be the blood flowing through a specified set of blood vessels. In other implementations, the spectral reference can generally be any other portion of the tissue sample 248 that has a consistent VN ratio, for example the highly reflective area on the surface of a blood vessel (rather than the blood itself).

At step 316, the near infrared channel is scaled based on spectral reference. This is done by calculating the theoretical VN ratio of the spectral reference within a specified layer of the tissue sample 248, which is generally assumed to be constant within the layer. After the VN ratio of the spectral reference has been calculated, the near infrared channel can then be scaled to ensure that the determined VN ratio of the spectral reference within the layer matches the calculated VN ratio.

In some implementations, only the near infrared channel is scaled. However, because the scaling process is just to ensure that the calculated VN ratio of the reference (e.g. the theoretical VN ratio) matches the measured VN ratio of the reference, one or both of the visible channel and the near infrared channel can be scaled. Thus for example, in some implementations only the visible channel is scaled, while in still other implementations both the visible channel and the near infrared channel are scaled.

At step 318, the VN ratio between the visible channel and the near infrared channel can be calculated for every pixel. Because the visible and near infrared channels were squared in step 312, the VN ratio is given by the expression $I_{VIS}^2/I_{NIR}^2$, rather than $I_{VIS}/I_{NIR}$.

FIG. 9A shows a cross-sectional image of the retina 10 from the near infrared channel, while FIG. 9B shows a cross-sectional image of the retina 10 from the visible channel. These cross-sectional images of a retina 10 illustrate the layer detection abilities of method 300. In both images of the retina 10, method 300 was used to identify the upper boundary 18A and the lower boundary 18B of the nerve fiber layer of the retina 10.

Figure 9C:
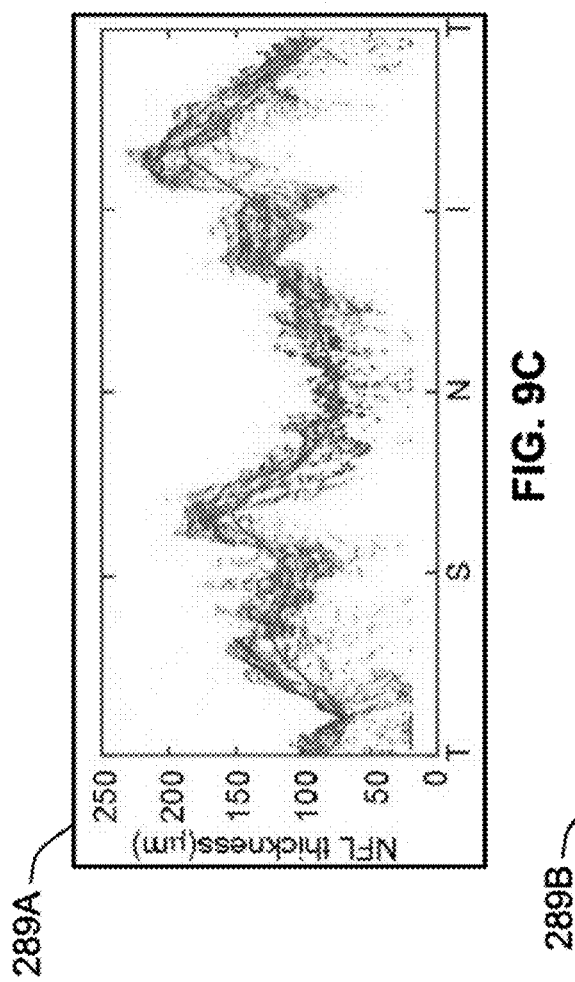
FIG. 9C is a plot of the thickness of the nerve fiber layer of the retina of FIG. 9A, according to some implementations of the present disclosure.
Figure 9D:
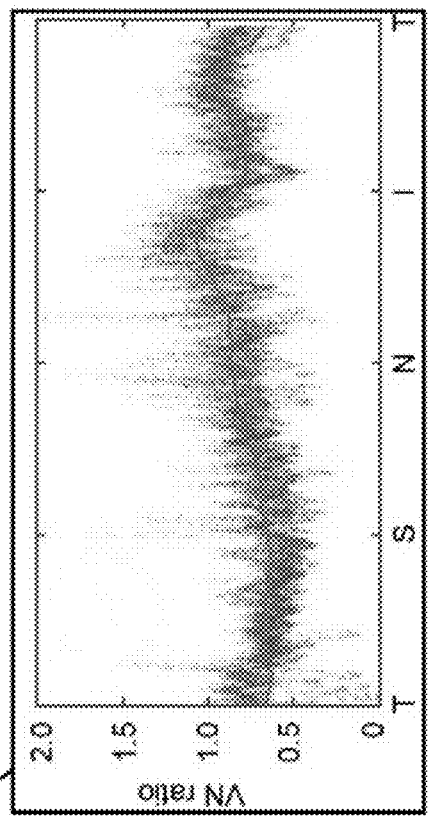
FIG. 9D is a plot of a visible-to-near-infrared ratio of the nerve fiber layer of the retina of FIG. 9A, according to some implementations of the present disclosure.

FIG. 9C shows a plot 289A of the thickness of the nerve fiber layer of the retina 10 that can be obtained using system 200. The thickness of the nerve fiber layer in microns is shown on the vertical axis and is plotted against a specific location within the retina 10, which is plotted on the horizontal axis. "T" refers to the temporal portion of the nerve fiber layer, which is nearest the temple. "N" refers to the nasal portion of the nerve fiber layer, which is nearest the nose. "S" refers to the upper portion of the nerve fiber layer. "I" refers to the lower portion of the nerve fiber layer. FIG. 9D shows a plot 289B of the VN ratio of the nerve fiber layer that can be obtained using system 200. The VN ratio is plotted against the location within the nerve fiber layer, with "T," "N," "S," and "I" referring to the temporal, superior, nasal, and inferior portions of the nerve fiber layer, respectively.

Figure 10A:
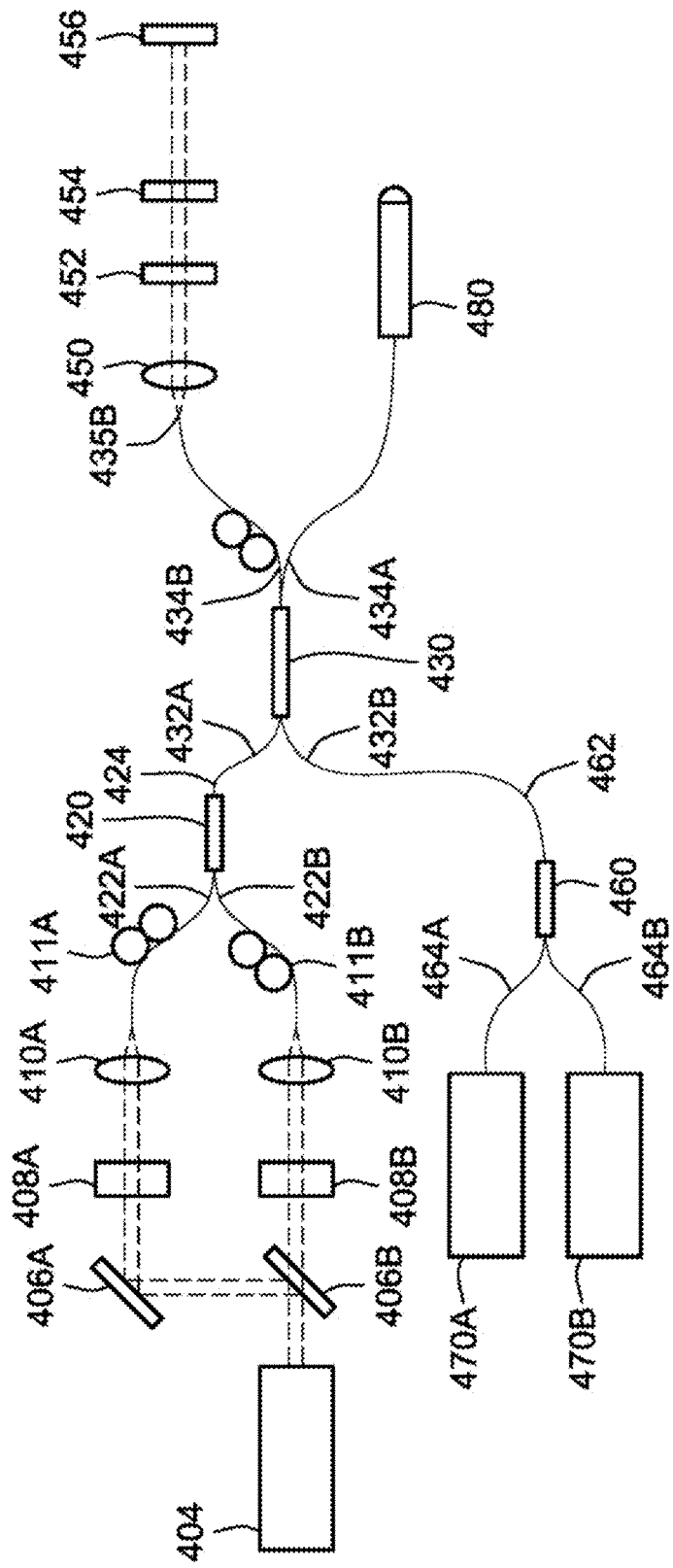
FIG. 10A is a system for using dual-band OCT with an optical probe to analyze a tissue sample, according to some implementations of the present disclosure.

Another implementation of a system for performing dual-band OCT is illustrated in FIG. 10A. System 400 utilizes a probe to direct visible and near infrared electromagnetic radiation to a tissue sample (not shown), instead of mirrors and lenses. The probe of system 400 can be used in situations that may require the probe to be inserted into a cavity, opening, or aperture in the tissue sample.

Similar to system 200 in FIG. 2A, system 400 is generally a more detailed version of system 100, and operates according to similar principles as system 100. System 400 includes a broad-spectrum electromagnetic radiation source 404 and dichroic mirrors 406A and 406B to generate visible electromagnetic radiation and near infrared electromagnetic radiation, similar to system 200. The near infrared electromagnetic radiation that reflects off dichroic mirror 406A propagates through a filter 408A and a linear polarizer 410. The filter 408A is used to filter out any unwanted wavelengths from the electromagnetic radiation reflecting off dichroic mirror 406A. The linear polarizer 410A ensures that the visible electromagnetic radiation only has one polarization. Finally, the visible electromagnetic radiation can also pass through a polarization controller 411A that can change the single polarization of the visible electromagnetic radiation. The near infrared electromagnetic radiation similarly propagates through a filter 408B, a linear polarizer 410B, and a polarization controller 411B to prepare the near infrared electromagnetic radiation for use in system 400.

The filtered and polarized visible electromagnetic radiation is received by a first input port 422A of a first wavelength-division multiplexer 420, while the filtered and polarized near infrared electromagnetic radiation is received by a second input port 422B if the first wavelength-division multiplexer 420. The first wavelength-division multiplexer 420 combines the visible and near infrared electromagnetic radiation, which is then emitted at an output port 424. The combined visible and near infrared electromagnetic radiation is directed to port 432A of fiber coupler 430, which in turn emits a sample beam at port 434A and a reference beam at port 434B. The fiber coupler 430 generally operates with the same principles as fiber coupler 230 in system 200, and can be a 95:5 splitter. Both the sample beam and the reference beam contain both visible electromagnetic radiation and near infrared electromagnetic radiation.

The reference beam 435B passes through a collimating lens 450, a variable neutral density filter 452, and a dispersion compensator 454, before reflecting off the reference mirror 256. The function of these components in system 400 is generally identical to the function of the corresponding components in system 200. The reference beam 435B then propagates back to the fiber coupler 430 where it is received by port 434B.

In system 400, port 434A of the fiber coupler 430 is optically coupled to an optical probe 480. The optical probe 480 can be placed adjacent to the tissue sample being analyzed in order to provide the reflected sample beam. In some implementations, the optical probe 480 is used to analyze colon tissue to detect markers of colon cancer, such as early increase in blood supply (EIBS) in colon tissue. Thus, system 400 can be used to perform micro-angiography of colon tissue to quantify colonic microvascular augmentation, which is generally an early indication of colon cancer. Thus, system 400 can generally be used to measure a variety of different features and properties related to blood vessels and capillaries in the tissue sample being analyzed, such as hemoglobin concentration, blood flow, oxygen saturation, and metabolic rate. Any alterations in these metabolic and microvascular properties can be indicative of colorectal cancer field carcinogenesis. The optical probe 480 allows system 400 to easily be used in vivo in both humans and animals.

Figure 10B:
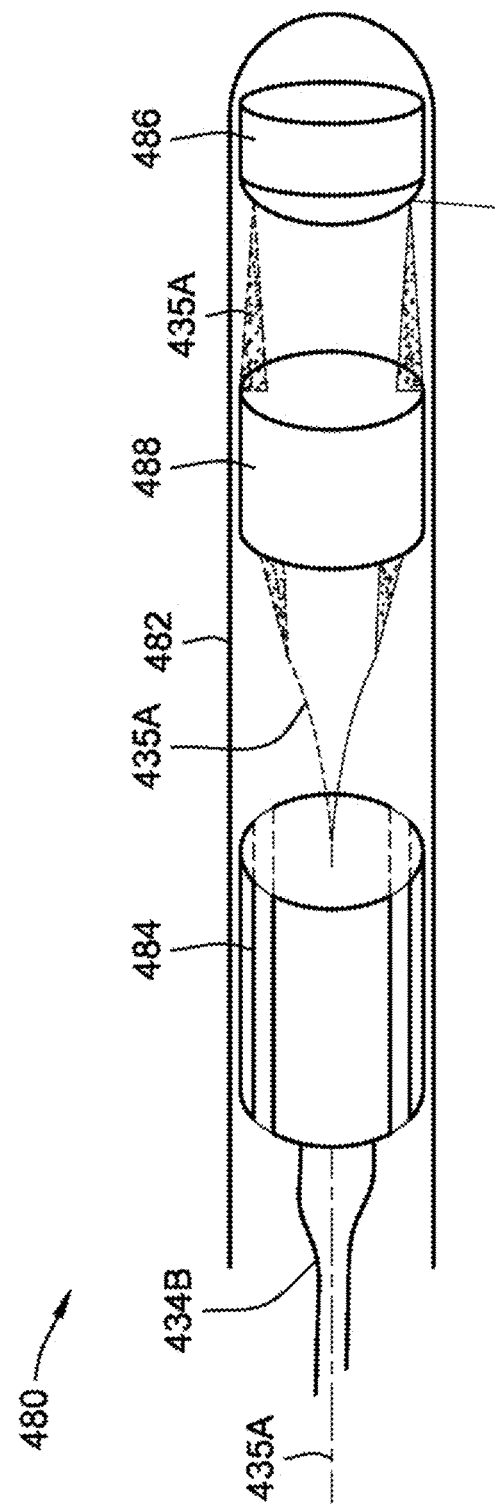
FIG. 10B is a perspective view of the optical probe of FIG. 10A, according to some implementations of the present disclosure.

FIG. 10B illustrates an implementation of the optical probe 480. When in use, the optical probe 480 is generally inserted into a body cavity, and thus uses rotational scanning in order to analyze the surrounding tissue. The fiber from port 434A of the fiber coupler 430 (which carries the sample beam 435A of electromagnetic radiation) is inserted into a housing 482 of the optical probe 480 and is coupled to a piezoelectric tube 484. The sample beam 435A of electromagnetic radiation is thus emitted from the piezoelectric tube 484. The piezoelectric tube 484 is configured to move or oscillate in response to an input. In some implementations, the piezoelectric tube 484 has four electrodes arranged in four separate quadrants. When the electrodes are driven by one or more sinusoidal voltages at or near the resonance frequency of the piezoelectric tube 484, the piezoelectric tube 484 moves in a fashion determined by the driving frequencies of the one or more sinusoidal voltages.

In this implementation, one pair of the four electrodes is driven by a first sinusoidal voltage, while a second pair of the four electrodes is driven by a second sinusoidal voltage. When the first and second sinusoidal voltages are offset by a phase shift of $\pi/2$, the piezoelectric tube 484 moves in a circular or rotational fashion. Because the fiber from port 434A is inserted into the housing and coupled to the piezoelectric tube 484, this causes the fiber itself to move in a circular or rotational fashion. In turn, the sample beam 435A of electromagnetic radiation is rotated in a circular pattern centered on the axis of the optical probe 480. The resonance frequency of the piezoelectric tube 484 (and thus the response to the driving voltage) can be adjusted by altering the length and weight of the piezoelectric tube 484. In some implementations, the piezoelectric tube 484 is designed to have a high resonance frequency for use with micro-angiography, but can also be driven at a non-resonance frequency for blood flow measurements.

The circular scanned sample beam 435A can pass through a spherical graded refractive index (grin) lens 488 that focuses the sample beam 435A to the peripheral edge of a spherical mirror 486, which reflects the sample beam 435A to the side wall of the housing 482. Then, as the piezoelectric tube 484 moves the fiber from output port 434A of the fiber coupler 430, the sample beam 435A rotates about the central axis of the tube to scan the tissue sample.

In some implementations, the mirror 486 has a thickness of about 2.0 mm and a radius of curvature of about 1.25 mm.

This allows the optical probe 480 to achieve a resolution of about 10.0 microns with a depth of view of about 1.0 mm. The optical probe 480 can have a diameter of equal to or less than about 2.0 mm, and achieve a rotational scanning rate of less than or equal to about 100 revolutions per second (rps).

In other implementations, the optical probe 480 could utilize a motor mounted within the optical probe 480 at a distal end thereof, or an external motor mounted to the optical probe 480 itself.

After the sample beam 435A is emitted from the mirror 486, it propagates to the tissue sample and reflects off various structures within the tissue sample back to the optical probe 480. The mirror 486 directs the reflected sample beam 435A back to the third port 434A of the fiber coupler 430. The fiber coupler 430 combines the reflected sample beam 435A and the reflected reference beam 435B in a similar fashion as fiber coupler 230 in system 200, and emits a single electromagnetic radiation signal at port 432B. This combined signal is received at the input port 462 of the second wavelength-division multiplexer 460, which separates the visible electromagnetic radiation and the near infrared electromagnetic radiation in the same manner as the second wavelength-division multiplexer 220 in system 200. The visible electromagnetic radiation from both the sample beam 435A and the sample beam 435B is emitted at the first output port 464A and sent to spectrometer 470A. The near infrared electromagnetic radiation from both the sample beam 435A and the sample beam 435B is emitted at the second output port 464B and sent to spectrometer 470A. The data from the spectrometers 470A and 470B can be used in a similar fashion as system 200 to analyze and create images of the tissue sample.

Dual-band OCT can be particularly helpful in analyzing and imaging colon tissue due to the different characteristics each band can help measure. Visible electromagnetic radiation generally beneficially increases spatial resolution and allows the system 400 to measure hemoglobin concentration and oxygen saturation due to the strong absorption spectra of hemoglobin within the visible range. However, visible electromagnetic radiation can easily be attenuated by the tissue sample, which can limit the penetration depth to about 0.5 mm. In turn, the electromagnetic radiation from the near infrared range can generally penetrate between about 1.0 mm and about 2.0 mm into the tissue, which allows for imaging of larger blood vessels. System 400 thus allows for the detection of the flow of red blood cells, and can be used to image single capillaries without the use of injected dye.

Figure 11:
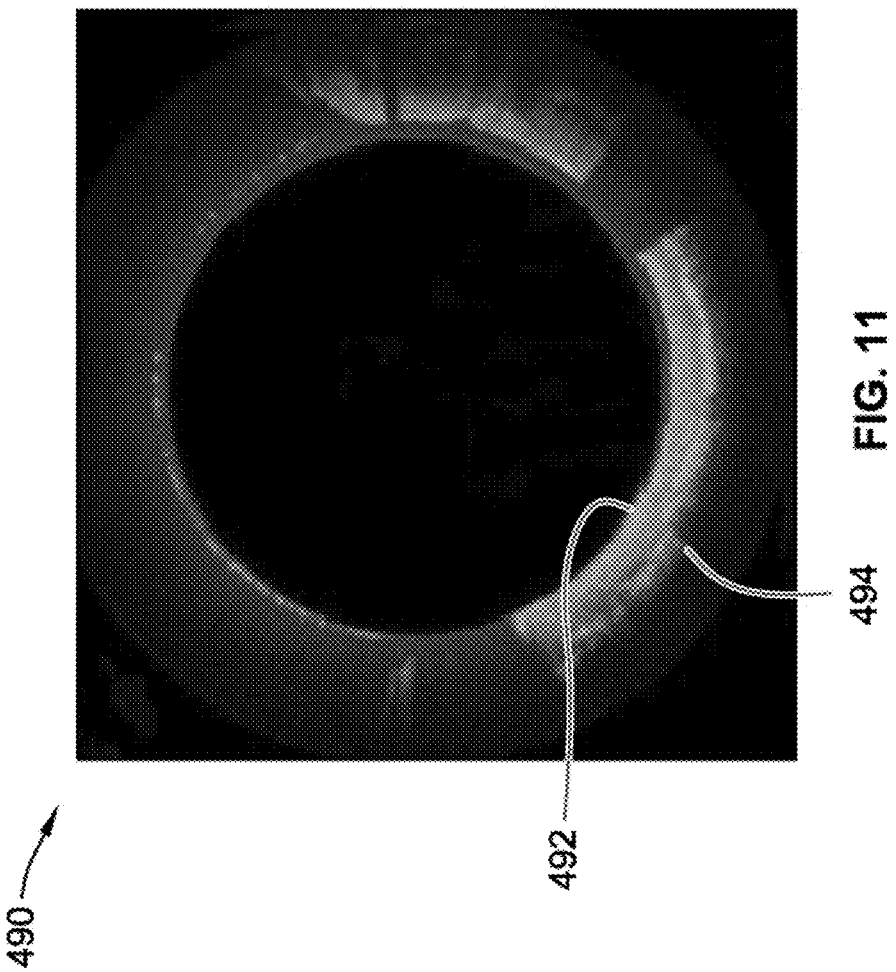
FIG. 11 is an image obtained using the system of FIG. 10, according to some implementations of the present disclosure.

FIG. 11 shows an example circular image 490 obtained using the optical probe 480 of system 400 that shows the rotational scanning capabilities of system 400. The circular image 490 in FIG. 11 is of the mucous membrane lining the inside of the mouth of a human subject, e.g., the oral mucosa. The image 490 is circular due to the way the scanning beam is emitted from the optical probe 480. The interior of the image 490 is dark, corresponding to the diameter of the optical probe 480 itself. The imaged tissue appears in a circle surrounding the dark interior. Visible in the image 490 is the epithelium 492 and the lamina propria 494. The epithelium 492 is generally the outer layer of the oral mucosa, and thus appears closer to the dark interior of image 490. The lamina propria 494 is located beneath the epithelium 492, and thus appears further away from the dark interior of image 490.

Generally, systems 100, 200, and 400 can all perform similar analyses on a variety of different tissues. The systems can be used to obtain 3D images utilizing only visible electromagnetic radiation, near infrared electromagnetic radiation, or both. The systems can also be used to generate 2D and 3D images showing the VN ratio of various structures within the tissue samples being analyzed, and to measure a wide variety of different parameters of the tissue samples.

Alternative Implementations

Alternative Implementation 1. A system for analyzing a tissue sample, comprising: a first optical combining component including a first input port configured to receive a first type of electromagnetic radiation, a second input port configured to receive a second type of electromagnetic radiation, and an output port configured to emit electromagnetic radiation that includes the first type of electromagnetic radiation and the second type of electromagnetic radiation; an optical hub, a first port of the optical hub being configured to receive the emitted electromagnetic radiation from the first optical combining component such that (i) a sample beam of electromagnetic radiation including the first type of electromagnetic radiation and the second type of electromagnetic radiation is emitted from a second port of the optical hub, is incident on an initial surface of the tissue sample, reflects off the tissue sample, propagates back to the second port, and is emitted from a third port of the optical hub, and (ii) a reference beam of electromagnetic radiation including the first type of electromagnetic radiation and the second type of electromagnetic radiation is emitted from a fourth port of the optical hub, reflects off a movable reference mirror spaced apart from the optical hub, propagates back to the fourth port, and is emitted from the third port of the optical hub; and a second optical combining component including an input port configured to receive the sample beam of electromagnetic radiation and the reference beam of electromagnetic radiation emitted from the third port of the optical hub such that (i) the electromagnetic radiation of the first type of both the sample beam and the reference beam is emitted at a first output port of the second optical combining component, and (ii) the electromagnetic radiation of the second type of both the sample beam and the reference beam is emitted at a second output port of the second optical combining component.

Alternative Implementation 2. The system of Alternative Implementation 1, wherein the first optical combining component and the second optical combining component are fiber-based wavelength-division multiplexers, and wherein the optical hub is a fiber coupler.

Alternative Implementation 3. The system of Alternative Implementation 2, wherein the fiber coupler is a 95:5 fiber coupler.

Alternative Implementation 4. The system of Alternative Implementation 3, wherein 5% of the emitted electromagnetic radiation incident on the first port of the fiber coupler is emitted from the second port of the fiber coupler as the reference beam of electromagnetic radiation, and wherein 95% of the emitted electromagnetic radiation incident on the first port of the fiber coupler is emitted from the fourth port of the fiber coupler.

Alternative Implementation 5. The system of Alternative Implementation 3, wherein 95% of the sample beam of electromagnetic radiation that reflects off the mirror and propagates back to the second port of the fiber coupler is emitted from the third port of the fiber coupler, and wherein 5% of the reference beam of electromagnetic radiation that reflects off the mirror and propagates back to the fourth port of the fiber coupler is emitted from the third port of the fiber coupler.

Alternative Implementation 6. The system of Alternative Implementation 1, wherein the first type of electromagnetic radiation and the second type of electromagnetic radiation have identical propagation modes.

Alternative Implementation 7. The system of Alternative Implementation 1, further comprising one or more spectrometers configured to compare: (i) a first optical path length difference between the first type electromagnetic radiation in the sample beam and the first type of electromagnetic radiation in the reference beam; and (ii) a second optical path length difference between the second type electromagnetic radiation in the sample beam and the second type of electromagnetic radiation in the reference beam.

Alternative Implementation 8. The system of Alternative Implementation 7, wherein the one or more spectrometers are further configured to determine a first intensity for the first type of electromagnetic radiation reflected off the tissue sample and the reference mirror, and a second intensity for the second type of electromagnetic radiation reflected off the tissue sample and the reference mirror.

Alternative Implementation 9. The system of Alternative Implementation 8, wherein the one or more spectrometers determine the first intensity and the second intensity for each of a plurality of depths into the tissue sample, each of the plurality of depths being measured relative the initial surface of the tissue sample onto which the sample beam of electromagnetic radiation is incident.

Alternative Implementation 10. The system of Alternative Implementation 1, further comprising one or more spectrometers configured to determine (i) a first intensity resulting from interference between the first type of electromagnetic radiation reflected off the tissue sample and first type of electromagnetic radiation reflected off the reference mirror, and (ii) a second intensity resulting from interference between the second type of electromagnetic radiation reflected off the tissue sample and the second type of electromagnetic radiation reflected off the reference mirror.

Alternative Implementation 11. The system of Alternative Implementation 10, wherein the first intensity and the second intensity are determined for a plurality of depths into the tissue sample, each of the plurality of depths being measured relative to the initial surface of the tissue sample onto which the sample beam of electromagnetic radiation is incident.

Alternative Implementation 12. The system of Alternative Implementation 1, wherein the tissue sample is a retina, a colon, or another organ.

Alternative Implementation 13. The system of Alternative Implementation 1, wherein the first type of electromagnetic radiation is electromagnetic radiation having one or more wavelengths in a first wavelength range, and wherein the second type of electromagnetic radiation is electromagnetic radiation having one or more wavelengths in a second wavelength range different than the first wavelength range.

Alternative Implementation 14. The system of Alternative Implementation 13, wherein the first wavelength range is between about 535 nanometers and about 600 nanometers, and wherein the second wavelength range is between about 785 nanometers and about 875 nanometers.

Alternative Implementation 15. The system of Alternative Implementation 13, wherein the first wavelength range is between about 520 nanometers and about 780 nanometers, and wherein the second wavelength range is between about 1200 nanometers and about 1300 nanometers.

Alternative Implementation 16. The system of Alternative Implementation 1, wherein the first type of electromagnetic radiation includes electromagnetic radiation having a center wavelength of about 565 nanometers, and wherein the second type of electromagnetic radiation includes electromagnetic radiation having a center wavelength of about 830 nanometers.

Alternative Implementation 17. The system of Alternative Implementation 1, wherein the first type of electromagnetic radiation is visible electromagnetic radiation, and wherein the second type of electromagnetic radiation is near-infrared electromagnetic radiation.

Alternative Implementation 18. The system of Alternative Implementation 17, wherein the electromagnetic radiation emitted from the first optical combining component includes visible electromagnetic radiation and near-infrared electromagnetic radiation.

Alternative Implementation 19. The system of Alternative Implementation 18, wherein the sample beam of electromagnetic radiation emitted from the second port of the optical hub includes visible electromagnetic radiation and near-infrared electromagnetic radiation.

Alternative Implementation 20. The system of Alternative Implementation 18, wherein the reference beam of electromagnetic radiation emitted from the fourth port of the optical hub includes visible electromagnetic radiation and near-infrared electromagnetic radiation.

Alternative Implementation 21. The system of Alternative Implementation 1, further comprising a first analysis device coupled to the first output of the second optical combining component, and a second analysis device coupled to the second output of the second optical combining component.

Alternative Implementation 22. The system of Alternative Implementation 21, wherein the first analysis device is a first spectrometer configured to compare the first type of electromagnetic radiation from the sample beam that reflected off the tissue sample and the first type of electromagnetic radiation from the reference beam that reflected off the reference mirror.

Alternative Implementation 23. The system of Alternative Implementation 22, wherein the second analysis device is a second spectrometer configured to compare the second type of electromagnetic radiation from the sample beam that reflected off the tissue sample and the second type of electromagnetic radiation from the reference beam that reflected off the reference mirror.

Alternative Implementation 24. The system of Alternative Implementation 1, further comprising one or more polarization components configured to cause the first type of electromagnetic radiation in both the sample beam and the reference beam, and the second type of electromagnetic radiation in both the sample beam and the reference beam, to have the same polarization.

Alternative Implementation 25. The system of Alternative Implementation 23, wherein the one or more polarization components includes at least one polarizing beam splitter to polarize electromagnetic radiation and at least one polarization controller to modify the polarization of the polarized electromagnetic radiation.

Alternative Implementation 26. The system of Alternative Implementation 1, further comprising a first electromagnetic radiation source configured to emit the first type of electromagnetic radiation, and a second electromagnetic radiation source configured to emit the second type of electromagnetic radiation.

Alternative Implementation 27. The system of Alternative Implementation 1, further comprising a broad-spectrum electromagnetic radiation source configured to emit electromagnetic radiation that includes the first type of electromagnetic radiation and the second type of electromagnetic radiation.

Alternative Implementation 28. The system of Alternative Implementation 27, wherein the broad-spectrum electromagnetic radiation source is a supercontinuum laser.

Alternative Implementation 29. The system of Alternative Implementation 27, wherein the electromagnetic radiation emitted by the broad-spectrum electromagnetic radiation source is divided by a dichroic mirror based on wavelength into a first portion of electromagnetic radiation that includes the first type of electromagnetic radiation and a second portion of electromagnetic radiation that includes the second type of electromagnetic radiation, the second portion of electromagnetic radiation being different than the first portion of electromagnetic radiation.

Alternative Implementation 30. The system of Alternative Implementation 29, wherein the first portion of electromagnetic radiation includes the first type of electromagnetic radiation and other types of electromagnetic radiation.

Alternative Implementation 31. The system of Alternative Implementation 30, further comprising one or more optical components to separate the first type of electromagnetic radiation from the other types of electromagnetic radiation.

Alternative Implementation 32. The system of Alternative Implementation 29, wherein the second portion of electromagnetic radiation includes only the second type of electromagnetic radiation.

Alternative Implementation 33. The system of Alternative Implementation 29, wherein the first portion of electromagnetic radiation includes visible electromagnetic radiation having one or more wavelengths within a visible wavelength range, and wherein the first type of electromagnetic radiation includes visible electromagnetic radiation having one or more wavelengths within a portion of the visible wavelength range.

Alternative Implementation 34. The system of Alternative Implementation 29, wherein the system further includes one or more prisms, the first portion of electromagnetic radiation being directed to the one or more prisms to separate the first portion of electromagnetic radiation into discrete components based on wavelength.

Alternative Implementation 35. The system of Alternative Implementation 34, further comprising a filter to remove discrete components of the first portion of electromagnetic radiation that do not correspond to the first type of electromagnetic radiation.

Alternative Implementation 36. The system of Alternative Implementation 29, wherein the dichroic mirror has a cut-off wavelength of about 650 nanometers.

Alternative Implementation 37. The system of Alternative Implementation 1, further comprising an achromatizing lens disposed between the second port of the optical hub and the tissue sample, the achromatizing lens configured to assist in simultaneously focusing both the first type of electromagnetic radiation and the second type of electromagnetic radiation of the sample beam on the tissue sample.

Alternative Implementation 38. The system of Alternative Implementation 37, wherein the achromatizing lens is a triplet lens including a first convex lens, a second concave lens, and a third convex lens.

Alternative Implementation 39. The system of Alternative Implementation 37, further comprising one or more optical components positioned between the achromatizing lens and the tissue sample configured to assist in steering the sample beam.

Alternative Implementation 40. The system of Alternative Implementation 39, wherein the one or more optical components includes a pair of galvanometer mirrors and a 2:1 telescope.

Alternative Implementation 41. The system of Alternative Implementation 1, wherein the initial surface of the tissue sample is an outer surface of the tissue sample.

Alternative Implementation 42. The system of Alternative Implementation 1, wherein at least a portion of the sample beam of electromagnetic radiation reflects off (i) the initial surface of the tissue sample, (ii) one or more structures within the tissue sample, or (iii) both (i) and (ii).

Alternative Implementation 43. The system of Alternative Implementation 1, further comprising an optical probe disposed adjacent to the tissue sample and coupled to the second port of the optical hub such that the sample beam of electromagnetic radiation propagates along the optical probe toward the tissue sample, reflects off the tissue sample, propagates along the optical probe back to the second port of the optical hub, and is emitted from the third port of the optical hub.

Alternative Implementation 44. The system of Alternative Implementation 43, wherein the optical probe includes a piezoelectric tube mounted and an optical fiber, a first end of the optical fiber being coupled to the second port of the optical hub, a second end of the optical fiber being coupled to the piezoelectric tube, the piezoelectric tube being configured to rotate within a housing to thereby cause the sample beam of electromagnetic radiation emitted from the optical fiber to rotate within the housing.

Alternative Implementation 45. The system of Alternative Implementation 44, wherein the optical probe further comprises a spherical lens and a spherical mirror, the optical fiber directing the sample beam of electromagnetic radiation to the spherical lens to focus the sample beam of electromagnetic radiation onto a peripheral edge of the spherical mirror and thereby cause the sample beam of electromagnetic radiation to directed to a side wall of the housing and toward the tissue sample.

Alternative Implementation 46. A method for analyzing a tissue sample, comprising: combining a first type of electromagnetic radiation and a second type of electromagnetic radiation; directing a sample beam of electromagnetic radiation that includes the first type of electromagnetic radiation and the second type of electromagnetic radiation to the tissue sample such that the sample beam of electromagnetic radiation reflects off the tissue sample; directing a reference beam of electromagnetic radiation that includes the first type of electromagnetic radiation and the second type of electromagnetic radiation to a mirror such that the reference beam of electromagnetic radiation reflects off the tissue sample; combining the reflected sample beam and the reflected reference beam; directing the first type of electromagnetic radiation from both the reflected sample beam and the reflected reference beam to a first analysis device; and directing the second type of electromagnetic radiation from both the reflected sample beam and the reflected reference beam to a second analysis device.

Alternative Implementation 47. The method of Alternative Implementation 46 further comprising: measuring a first intensity of an interference pattern between the first type of electromagnetic radiation from the sample beam to the first type of electromagnetic radiation from the reference beam; and measuring a second intensity of an interference pattern between the second type of electromagnetic radiation from the sample beam to the second type of electromagnetic radiation from the reference beam.

Alternative Implementation 48. The method of Alternative Implementation 47, further comprising correcting at least one of the measured first intensity or the measured second intensity based at least on: (i) roll-off performance, (ii) background noise, (iii) reference objects within the tissue sample, or (iv) any combination of (i)-(iii).

Alternative Implementation 49. The method of Alternative Implementation 46, wherein the tissue sample is a retina, a colon, or another organ.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention. It is also contemplated that additional embodiments according to aspects of the present invention may combine any number of features from any of the embodiments described herein.

What is claimed is:

1. A system for analyzing a tissue sample, comprising:
   a first optical combining component including a first input port configured to receive first electromagnetic radiation, a second input port configured to receive second electromagnetic radiation, and an output port configured to emit electromagnetic radiation that includes the first electromagnetic radiation and the second electromagnetic radiation;
   an optical hub, a first port of the optical hub being configured to receive the emitted electromagnetic radiation from the first optical combining component such that
   (i) a sample beam of electromagnetic radiation including the first electromagnetic radiation and the second electromagnetic radiation is emitted from a second port of the optical hub, is incident on an initial surface of the tissue sample, reflects off the tissue sample, propagates back to the second port, and is emitted from a third port of the optical hub, and
   (ii) a reference beam of electromagnetic radiation including the first electromagnetic radiation and the second electromagnetic radiation is emitted from a fourth port of the optical hub, reflects off a movable reference mirror spaced apart from the optical hub, propagates back to the fourth port, and is emitted from the third port of the optical hub;
   a second optical combining component including an input port configured to receive the sample beam of electromagnetic radiation and the reference beam of electromagnetic radiation emitted from the third port of the optical hub such that (i) the first electromagnetic radiation of both the sample beam and the reference beam is emitted at a first output port of the second optical combining component, and (ii) the second electromagnetic radiation of both the sample beam and the reference beam is emitted at a second output port of the second optical combining component;
   a first spectrometer configured to an intensity of a first interference pattern between the first electromagnetic radiation of the sample beam and the first electromagnetic radiation of the reference beam; and
   a second spectrometer configured to determine an intensity of a second interference pattern between the second electromagnetic radiation of the sample beam and the second electromagnetic radiation of the reference beam,
   wherein for each voxel of the tissue sample, a ratio of (i) the intensity of the first interference pattern to (ii) the intensity of the second interference pattern is determined.

2. The system of claim 1, wherein the first optical combining component and the second optical combining component are fiber-based wavelength-division multiplexers, and wherein the optical hub is a fiber coupler.

3. The system of claim 2, wherein the fiber coupler is a 95:5 fiber coupler.

4. The system of claim 3, wherein 5% of the emitted electromagnetic radiation incident on the first port of the fiber coupler is emitted from the second port of the fiber coupler as the sample beam of electromagnetic radiation, and wherein 95% of the emitted electromagnetic radiation incident on the first port of the fiber coupler is emitted from the fourth port of the fiber coupler as the reference beam of electromagnetic radiation.

5. The system of claim 3, wherein 95% of the sample beam of electromagnetic radiation that reflects off the tissue sample and propagates back to the second port of the fiber coupler is emitted from the third port of the fiber coupler, and wherein 95% of the reference beam of electromagnetic radiation that reflects off the movable reference mirror and propagates back to the fourth port of the fiber coupler is emitted from the third port of the fiber coupler.

6. The system of claim 1, wherein the first electromagnetic radiation and the second electromagnetic radiation have identical propagation modes.

7. The system of claim 1, wherein the intensity of the first interference pattern and the intensity of the second interference pattern are determined for a plurality of depths into the tissue sample, each of the plurality of depths being measured relative to the initial surface of the tissue sample onto which the sample beam of electromagnetic radiation is incident.

8. The system of claim 1, wherein the tissue sample is a retina, a colon, or another organ.

9. The system of claim 1, wherein the first electromagnetic radiation is electromagnetic radiation having one or more wavelengths in a first wavelength range, and wherein the second electromagnetic radiation is electromagnetic radiation having one or more wavelengths in a second wavelength range different than the first wavelength range.

10. The system of claim 1, wherein the first electromagnetic radiation is visible electromagnetic radiation, and wherein the second electromagnetic radiation is near-infrared electromagnetic radiation.

11. The system of claim 10, wherein the electromagnetic radiation emitted from the first optical combining component includes visible electromagnetic radiation and near-infrared electromagnetic radiation.

12. The system of claim 11, wherein the sample beam of electromagnetic radiation emitted from the second port of the optical hub includes visible electromagnetic radiation and near-infrared electromagnetic radiation, and wherein the reference beam of electromagnetic radiation emitted from the fourth port of the optical hub includes visible electromagnetic radiation and near-infrared electromagnetic radiation.

13. The system of claim 1, further comprising one or more polarization components configured to cause the first electromagnetic radiation in both the sample beam and the reference beam, and the second electromagnetic radiation in both the sample beam and the reference beam, to have the same polarization, the one or more polarization components including at least one polarizing beam splitter to polarize electromagnetic radiation and at least one polarization controller to modify the polarization of the polarized electromagnetic radiation.

14. The system of claim 1, further comprising a first electromagnetic radiation source configured to emit the first electromagnetic radiation, and a second electromagnetic radiation source configured to emit the second electromagnetic radiation.

15. The system of claim 1, further comprising a broad-spectrum electromagnetic radiation source configured to emit electromagnetic radiation that includes the first electromagnetic radiation and the second electromagnetic radiation.

16. The system of claim 15, wherein the broad-spectrum electromagnetic radiation source is a supercontinuum laser.

17. The system of claim 15, wherein the electromagnetic radiation emitted by the broad-spectrum electromagnetic radiation source is divided by a dichroic mirror based on wavelength into a first portion of electromagnetic radiation that includes the first electromagnetic radiation and a second portion of electromagnetic radiation that includes the second electromagnetic radiation, the second portion of electromagnetic radiation being different than the first portion of electromagnetic radiation.

18. The system of claim 1, further comprising an achromatizing lens disposed between the second port of the optical hub and the tissue sample, the achromatizing lens configured to assist in simultaneously focusing both the first electromagnetic radiation and the second electromagnetic radiation of the sample beam on the tissue sample.

19. The system of claim 18, wherein the achromatizing lens is a triplet lens including a first convex lens, a second concave lens, and a third convex lens.

20. The system of claim 1, wherein the initial surface of the tissue sample is an outer surface of the tissue sample.

21. The system of claim 1, wherein at least a portion of the sample beam of electromagnetic radiation reflects off (i) the initial surface of the tissue sample, (ii) one or more structures within the tissue sample, or (iii) both (i) and (ii).

22. The system of claim 1, further comprising an optical probe disposed adjacent to the tissue sample and coupled to the second port of the optical hub such that the sample beam of electromagnetic radiation propagates along the optical probe toward the tissue sample, reflects off the tissue sample, propagates along the optical probe back to the second port of the optical hub, and is emitted from the third port of the optical hub.

23. The system of claim 22, wherein the optical probe includes a piezoelectric tube mounted and an optical fiber, a first end of the optical fiber being coupled to the second port of the optical hub, a second end of the optical fiber being coupled to the piezoelectric tube, the piezoelectric tube being configured to rotate within a housing to thereby cause the sample beam of electromagnetic radiation emitted from the optical fiber to rotate within the housing.

24. The system of claim 23, wherein the optical probe further comprises a spherical lens and a spherical mirror, the optical fiber directing the sample beam of electromagnetic radiation to the spherical lens to focus the sample beam of electromagnetic radiation onto a peripheral edge of the spherical mirror and thereby cause the sample beam of electromagnetic radiation to directed to a side wall of the housing and toward the tissue sample.

25. A method for analyzing a tissue sample, comprising:
combining first electromagnetic radiation and second electromagnetic radiation;
directing a sample beam of electromagnetic radiation that includes the first electromagnetic radiation and the second electromagnetic radiation to the tissue sample such that the sample beam of electromagnetic radiation reflects off the tissue sample;
directing a reference beam of electromagnetic radiation that includes the first electromagnetic radiation and the second electromagnetic radiation to a mirror such that the reference beam of electromagnetic radiation reflects off the mirror;
combining the reflected sample beam and the reflected reference beam;
directing the first electromagnetic radiation from both the reflected sample beam and the reflected reference beam to a first analysis device;
directing the second electromagnetic radiation from both the reflected sample beam and the reflected reference beam to a second analysis device;
measuring an intensity of a first interference pattern between the first electromagnetic radiation from the sample beam and the first electromagnetic radiation from the reference beam;
measuring an intensity of a second interference pattern between the second electromagnetic radiation from the sample beam and the second electromagnetic radiation from the reference beam; and
for each voxel of the tissue sample, determining a ratio of (i) the intensity of the first interference pattern to (ii) the intensity of the second interference pattern.

26. The method of claim 25, further comprising correcting both the measured intensity of the first interference pattern and the measured intensity of the second interference pattern based at least on: (i) roll-off performance, (ii) background noise, (iii) reference objects within the tissue sample, or (iv) any combination of (i)-(iii).

27. The method of claim 25, wherein the tissue sample is a retina, a colon, or another organ.

28. The method of claim 25, further comprising scaling the determined ratio based on a spectral reference to correct for variations between the first interference pattern and the second interference pattern.

29. The method of claim 28, wherein the spectral reference is a surface of a blood vessel in the tissue sample.

30. The method of claim 25, further comprising, for each voxel in the tissue sample, squaring the intensity of the first interference pattern and the intensity of the second interference pattern, and wherein determining the ratio of (i) the intensity of the first interference pattern to (ii) the intensity of the second interference pattern includes determining a ratio of (i) the squared intensity of the first interference pattern to (ii) the square intensity of the second interference pattern.

* * * * *